United States Patent
Hakkarainen et al.

(10) Patent No.: US 12,121,624 B2
(45) Date of Patent: Oct. 22, 2024

(54) DISINFECTION METHOD AND DISINFECTION DEVICE

(71) Applicant: CLEAMIX OY, Riistavesi (FI)

(72) Inventors: Harri Hakkarainen, Tallinn (EE); Panu Wilska, Kauniainen (FI)

(73) Assignee: CLEAMIX OY, Riistavesi (FI)

(*) Notice: Subject to any disclaimer, the term of this patent is extended or adjusted under 35 U.S.C. 154(b) by 796 days.

(21) Appl. No.: 17/194,964

(22) PCT Filed: Sep. 5, 2019

(86) PCT No.: PCT/FI2019/050636
§ 371 (c)(1),
(2) Date: Mar. 8, 2021

(87) PCT Pub. No.: WO2020/049224
PCT Pub. Date: Mar. 12, 2020

(65) Prior Publication Data
US 2021/0386890 A1    Dec. 16, 2021

(30) Foreign Application Priority Data

Sep. 9, 2018 (FI) ..................................... 20187119
Sep. 9, 2018 (FI) ..................................... 20187121
(Continued)

(51) Int. Cl.
*A61L 2/20* (2006.01)

(52) U.S. Cl.
CPC ........... *A61L 2/208* (2013.01); *A61L 2202/11* (2013.01); *A61L 2202/17* (2013.01); *A61L 2202/25* (2013.01)

(58) Field of Classification Search
CPC ............. A61L 2202/11; A61L 2202/17; A61L 2202/25; A61L 2/208
See application file for complete search history.

(56) References Cited

U.S. PATENT DOCUMENTS

| 2,751,338 A | 6/1956 | Schwemberger |
| 6,120,730 A | 9/2000 | Palaniappan et al. |

(Continued)

FOREIGN PATENT DOCUMENTS

| CN | 1032297 | 4/1989 |
| CN | 108452360 | 8/2018 |

(Continued)

OTHER PUBLICATIONS

Finnish Search Report for 20187119 dated Apr. 5, 2019, 2 pages.
(Continued)

*Primary Examiner* — Sean E Conley
(74) *Attorney, Agent, or Firm* — Nixon & Vanderhye PC

(57) ABSTRACT

The invention relates to a disinfection method to be used for cleaning. The invention is characterized in that hydrogen peroxide ($H_2O_2$) is drained/transferred from one or more tanks (16) by a liquid pressure created by one or more pumps or gravity, through one or more draining pipes (6) to one or more draining devices (5), which draining device (5) drains hydrogen peroxide to one or more onto one or more evaporation top surfaces (4*ea*) of an evaporation member (4*e*) of a warming/heating device (4), the evaporation top surface (4*ea*) is at an evaporation angle (4*ej*) of 1 to 30 degrees in relation to the horizontal plane so that the end on the draining device (5) side draining end (4*c*) is higher than a gas discharge end (4*d*) at the opposite end of the draining device (5) of the warming/heating device (4), whereby hydrogen peroxide spreads by gravity on the evaporation member 4*e* where the hydrogen peroxide ($H_2O_2$) turns into hydrogen peroxide gas by means of which hydrogen peroxide gas disinfection is performed, the evaporation member (4*e*) consist of one or more braidings or mat or fabric that is either in its entirety or partly a mixture of the aforementioned materials such as nylon or polyester (PET) or PEN (Continued)

Figure 1:
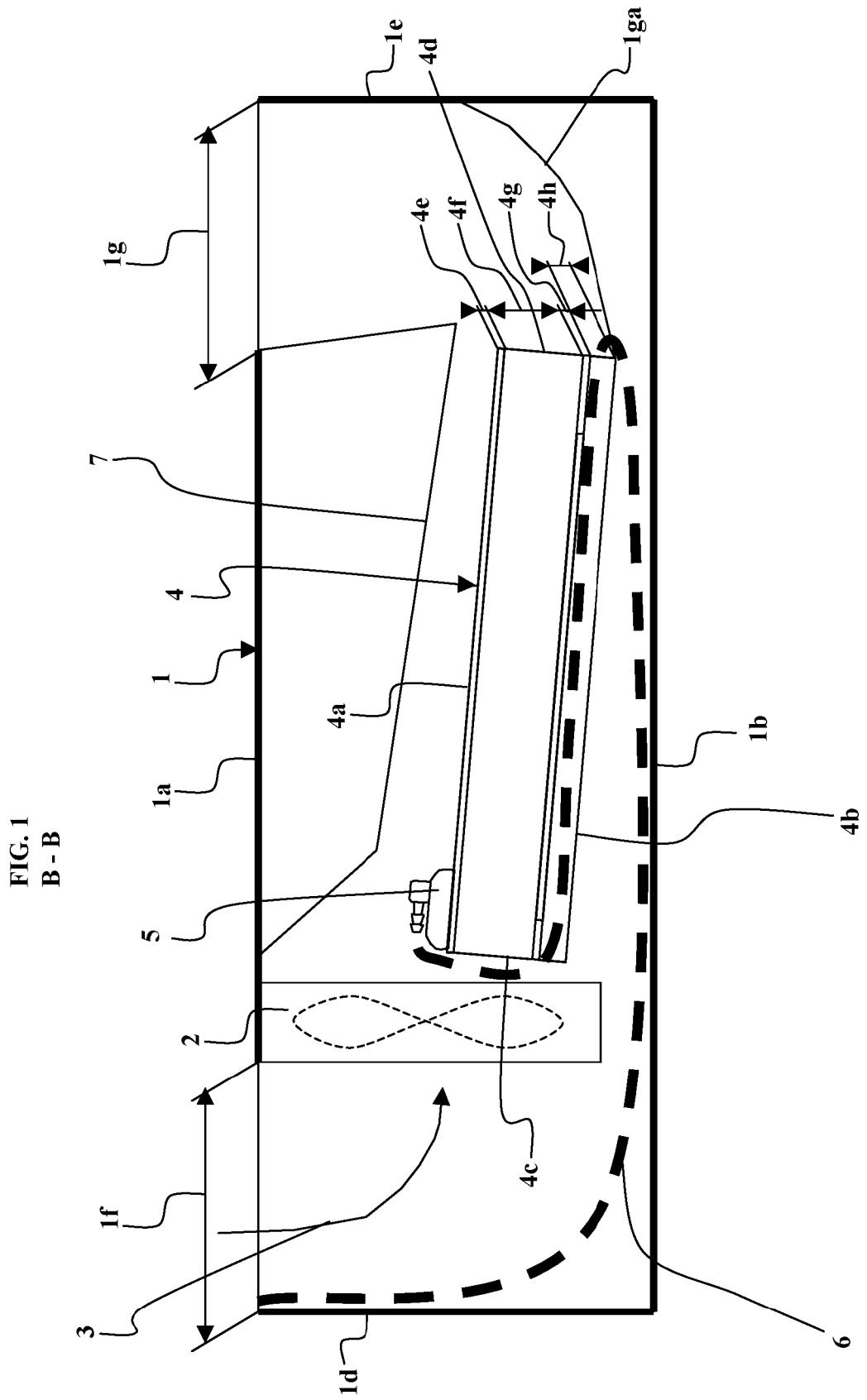

fibre (Pentex) or kevlar or technora or twaron or spektri or dyneema or cetran or zylon (PBO) or vecran or fibre glass braiding or carbon fibre or perforated plate or metal net or aluminium oxide.

12 Claims, 23 Drawing Sheets

(30) Foreign Application Priority Data

Sep. 9, 2018 (FI) .................................... 20187128
Aug. 9, 2019 (FI) .................................... 20197109

(56) References Cited

U.S. PATENT DOCUMENTS

| | | |
|---|---|---|
| 2003/0031588 A1 | 2/2003 | Schur |
| 2004/0089369 A1 | 5/2004 | Armbruster et al. |
| 2004/0265459 A1 | 12/2004 | Lark et al. |
| 2017/0246030 A1 | 8/2017 | Lewis |

FOREIGN PATENT DOCUMENTS

| | | |
|---|---|---|
| DE | 10 2016 118 475 | 3/2018 |
| EP | 1 738 777 | 1/2007 |
| EP | 2 650 023 | 10/2013 |
| JP | S63-011163 | 1/1988 |
| JP | 05-310228 | 11/1993 |
| JP | H09-294805 | 11/1997 |
| JP | 2003-339829 | 12/2003 |
| JP | 2004-532087 | 10/2004 |
| JP | 2005-065882 | 3/2005 |
| JP | 2016-221078 | 12/2016 |
| JP | 2018-089064 | 6/2018 |
| WO | 2017/137665 | 8/2017 |
| WO | 2017/218832 | 12/2017 |

OTHER PUBLICATIONS

Finnish Search Report for 20187121 dated Apr. 5, 2019, 2 pages.
Finnish Search Report for 20187128 dated Apr. 5, 2019, 2 pages.
Finnish Search Report for 20197109 dated Mar. 19, 2020, 2 pages.
International Search Report for PCT/FI2019/050636 dated Dec. 20, 2019, 5 pages.
Written Opinion of the ISA for PCT/FI2019/050636 dated Dec. 20, 2019, 9 pages.
Notice of Grounds for Rejection issued on Jan. 31, 2023 in corresponding Korean Application No. 10-2021-7010399 (with English translation), 12 pages.
Office Action issued on Apr. 18, 2022 in corresponding Chinese Application No. 201980058609.5 (with translation), 11 pages.
Office Action mailed on Apr. 22, 2022 in corresponding Japanese Application No. 2021-537511 (with translation), 6 pages.

B - B

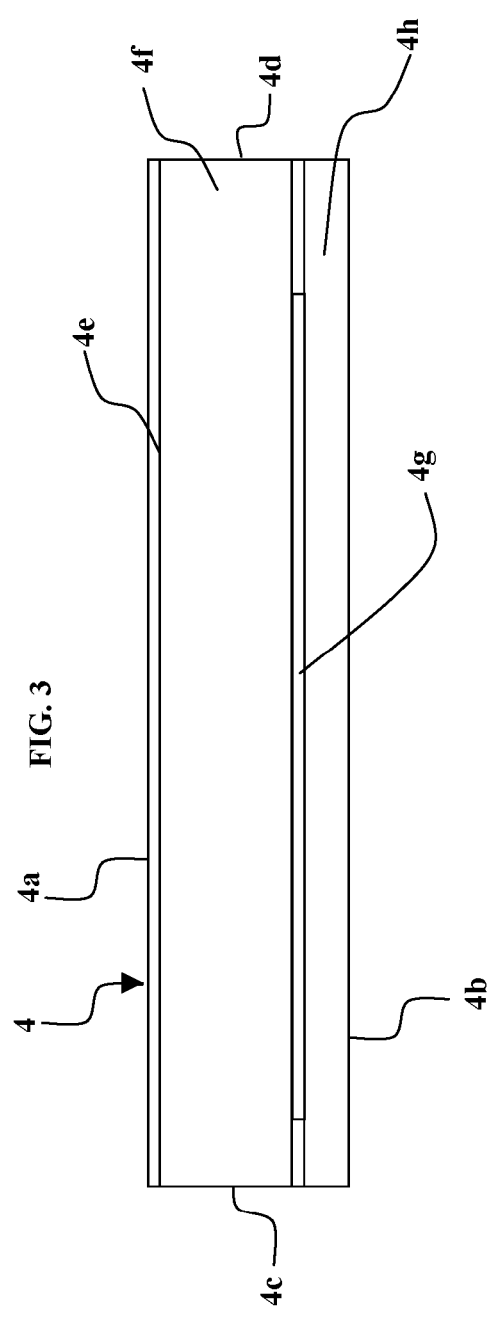
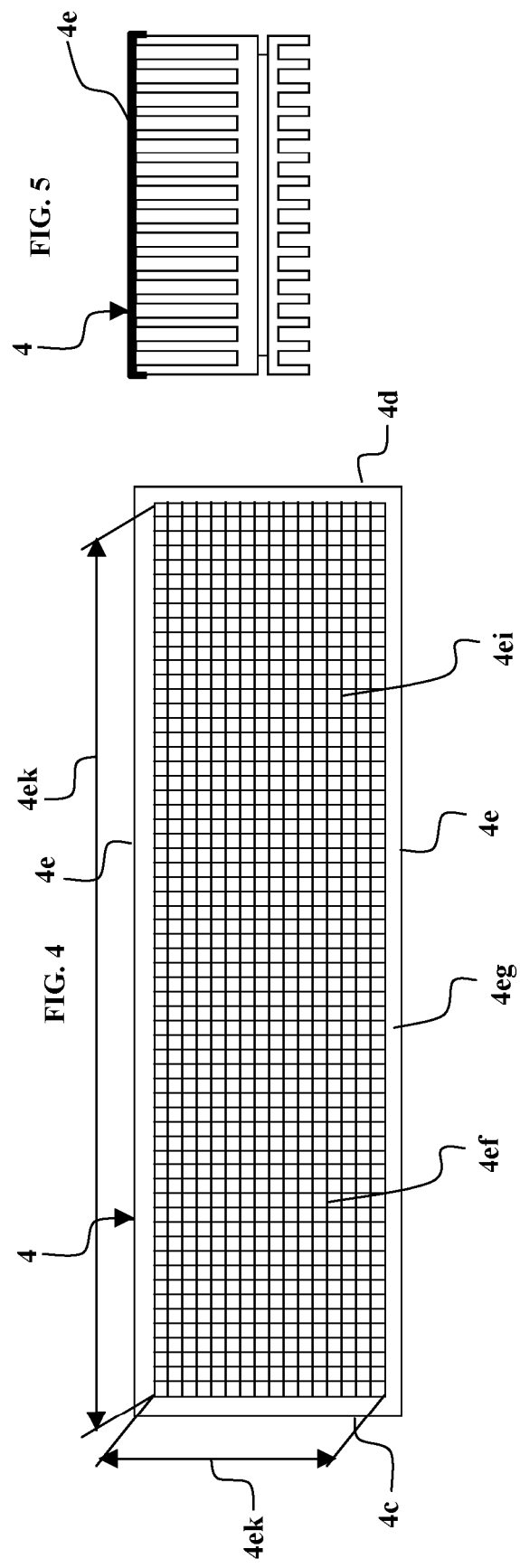

A - A

DISINFECTION METHOD AND DISINFECTION DEVICE

CROSS-REFERENCE TO RELATED APPLICATIONS

This application is the U.S. national phase of International Application No. PCT/FI2019/050636 filed Sep. 5, 2019 which designated the U.S. and claims priority to FI 20187119 filed Sep. 9, 2018, FI 20187121 filed Sep. 9, 2018, FI 20187128 filed Sep. 9, 2018 and FI 20197109 filed Aug. 9, 2019, the entire contents of each of which are hereby incorporated by reference.

OBJECT OF THE INVENTION

The present invention relates to a disinfection method for use for cleaning in targets to be cleaned, such as the living environment of people and animals, as well as in the growing/storage environment of human and animal food, or in the transport/moving environment of people and animals. The invention additionally relates to a disinfecting device for use for cleaning in targets to be cleaned, such as the living environment of people and animals, as well as in the growing/storage environment of human and animal food, or in the transport/moving environment of people and animals.

TARGETS TO BE CLEANED IN MORE DETAIL

Used for exterminating microbes and bacteria. Any premises or things are cleaned, which have been contaminated by microbes, bacteria, or germ growth, such as hospitals Disinfecting is needed:
At hospitals for cleaning the premises. For controlling hospital bacteria and contagious diseases.
For cleaning ambulances and patient transportation equipment.
For cleaning the transport equipment and other gear of fire and rescue services.
For cleaning air conditioning systems of buildings.
For cleaning laboratory spaces (e.g. safety cabinets).
In food industry, for cleaning rooms, machines, and transport equipment.
Manufacture of biofuels—Reducing product loss. Contaminated target, only, is cleaned.
In defence forces, bioterrorism, biowarfare, the contaminated targets/equipment are cleaned.
In security applications, safety applications, the transport equipment and other gear, such as clothing, are cleaned.
Animal diseases/animal production premises. Contaminated premises are cleaned.
Transport logistics (ships, aeroplanes etc.), contaminated transport equipment is cleaned.
For pest control and micro-organisms control, vermin control, such as ant control, silver fish control, etc.

Common nouns for nuisances to be disinfected and their targets.
Bacteria, microbes, viruses, and pests/vermin. For example at hospitals, households, shops, laboratories, premises/spaces used by people and animals in general.
Bacteria, microbes, viruses, and pests/vermin. Cleaning of premises/areas after contamination by, for example, biological warfare/terrorism. Following a natural disaster (destroying living material, for example, for disinfecting bodies, whereby bodies cannot spread bacteria, microbes, or viruses).
Bacteria, microbes, viruses, and pests/vermin. Different kinds of channels for moving material, route networks, tunnels for transporting material, such as ventilation channels, water pipelines (when empty), sewer pipes.
Bacteria, microbes, viruses, and pests/vermin. Vehicles on land, water, and air, such as ambulance vehicles, firefighting vehicles, buses, cars, aeroplanes, ships, rockets, work machines.
Bacteria, microbes, viruses, and pests/vermin.

PRIOR ART

Currently, weak hydrogen peroxide is used for cleaning, by spraying the substance in question to the space directly onto the target(s) to be cleaned.

The problem is non-spreading, does not spread everywhere. Corrosion effect, because hydrogen peroxide is corrosive in its liquid form. Adjusting the amount of hydrogen peroxide content is difficult, because dosing hydrogen peroxide evenly on the surface to be cleaned is impossible to achieve. The hydrogen peroxide content is uneven, resulting in a varying cleaning time. Close to the moisture point, an imprecise dosage leads to the hydrogen peroxide condensing back to liquid, which leads to liquid hydrogen peroxide remaining on the cleaned target, corroding the cleaned target. Cleaning by hydrogen peroxide is presently slow, imprecise and consequently expensive work. In addition, part of the cleaned target will not be evenly cleaned, if at all.

From publication JP 2003339829 A (Figure, machine translation paragraphs [0013]-[0024]), a disinfection method and disinfection device for the purpose of cleaning are known. In the method, hydrogen peroxide is sprayed from a container at a liquid pressure created by a pump through a spraying member to an evaporation member where also a hot carrier gas stream is led. In the evaporation member, hydrogen peroxide turns into hydrogen peroxide gas. To blow the carrier gas stream, a blower is used.

In publication JP 2003339829 A, the evaporation member is formed of a long, straight and open space with closed walls, the evaporation member being referred to as a flushing area/zone in the publication, to which flushing area/zone air and hydrogen peroxide solution are mixedly sprayed, due to which hydrogen peroxide comes as small droplets. The flushing area/zone is heated from the outside by an electric heater. From the machine translation, "the flushing area/zone, where downstream of a spray nozzle the electric heater is installed on flushing area/zone with an enlarged diameter, the electric heater is sufficiently long, the hydrogen peroxide solution evaporates into fine particles. Furthermore, the flushing area/zone is cylindrical or trumpet shaped, when viewed from the side, and is preferably vertically or horizontally. The flushing area/zone has no evaporation surface.

From publication EP2650023A1 (the entire publication; in particular paragraphs [0014]-[0024]; figures), a disinfection method and disinfection device for cleaning are known. In the method, hydrogen peroxide is sprayed from a tank at a liquid pressure produced by a pump through a spraying member to a evaporation member where also a hot carrier gas stream is led. In the evaporation member, hydrogen peroxide turns into hydrogen peroxide gas. FIG. 4, in particular, shows that the evaporation member is a closed tank that has no evaporation surface inside.

From publication US2004265459A1 (paragraphs [0006]-[0009], [0011], [0065]-[0068]; figure), a disinfection method and disinfection device for cleaning are known. In the method, a disinfectant (such as hydrogen peroxide) is sprayed from a tank at a liquid pressure produced by a pump through a spraying member to a evaporation member where also hot carrier gas stream is led. In the evaporating member, hydrogen peroxide is vaporized. In the publication is not mentioned that expressly a blower is used for blowing hot carrier gas. FIG. 1, in particular, shows that the evaporation member is a closed container that does not have any evaporation surface inside, just guide plates to mix the carrier gas and acetic acid.

In all the publications JP 2003339829 A, EP2650023A1 and US2004265459A1, the evaporation member is formed of a closed tank-like structure inside the tank-like structure of which there is no evaporation surface or means. In all the publications JP 2003339829 A, EP2650023A1 and US2004265459A1, hydrogen peroxide is sprayed by means of a liquid pressure created by a pump to an evaporation member where the hydrogen peroxide is vaporised.

OBJECT OF THE INVENTION

The object is that disinfection is carried out by hydrogen peroxide gas ($H_2O_2$), whereby no corrosion takes place, because hydrogen peroxide ($H_2O_2$) is not corrosive in the gaseous state.

The above disadvantages may be eliminated and the above goals be reached by the inventive disinfection method which is characterised by what is disclosed in the characterising part of claim 1, and the preferred embodiments of the methods are disclosed in claims 2 to 14. The disinfection device according to the invention is characterised by what is disclosed in the characterizing part of claim 15, and the preferred embodiments of a fastening element are disclosed in dependent claims 16 to 19.

As the most important benefits of the invention, it may be mentioned that the invented disinfection method provides a precise dosage of hydrogen peroxide gas on a target to be cleaned. The exact amount of hydrogen peroxide may be precisely dosed by draining hydrogen peroxide from one or more nozzles as a liquid stream on one or more warming/heating devices having one or more evaporation members which is the evaporation member. The evaporation member is the upper part of the warming/heating device, on the top surface of which to a draining end hydrogen peroxide is drained from one or more draining devices. The evaporation member consist of a fibreglass braiding. The evaporation top surface of the evaporation member is at an evaporation angle of 1 to 30 degrees, as seen from the side, so that an evaporation draining end higher than an evaporation gas end, whereby hydrogen peroxide drains downhill and is evenly spread on the entire evaporation top surface of the evaporation member following the draining device on which evaporation top surface hydrogen peroxide is gasified into hydrogen peroxide gas by means of which hydrogen peroxide gas cleaning is best performed controllably by one or more blow channels/blow pipes. The shape of the cross-section of the blow channel may differ from round, the cross-section may have a known shape such as a square, rectangle, oval, triangle, polygon etc. On the evaporation top surface, hydrogen peroxide evaporates fast into hydrogen peroxide gas as the warming member under-side of the evaporation surface warms up the evaporation surface. The airflow on the top side the evaporation surface is faster than the airflow under-side, whereby hydrogen peroxide gasifies fast, because the faster airflow on the top side tends to suck the vaporizing hydrogen peroxide with it. The airflow on the top side of the evaporation surface is colder than the airflow under side, due to which airflow swirls, so-called turbulence, is created on the top side of the evaporation member, which speeds up the gasifying of hydrogen peroxide. It is obvious that the use of the invented disinfection method results in great cost savings in cleaning.

General Information on Hydrogen Peroxide (Wikipedia)
https://fi.wikipedia.org/wiki/Vetyperoksidi#Aiheesta_muualla Hydrogen oxide (sometimes hydrogen superoxide) $H_2O_2$ is one of the oxides of hydrogen, whose CAS number is 7722-84-1. The other, more common oxide of hydrogen, is water ($H_2O$).

Properties

Hydrogen peroxide is a strongly oxidising agent. When warmed, it decomposes into water and oxygen whereby energy is released in the process at the same time. Some metals and impurities act as catalysts of the decomposing process. Hydrogen peroxide liquid may be stabilized with, for example phosphorus, sulphur, boron, or citric acid, acetanilide, or acetophenetide when the aim is to slow down the decomposing process.

Hydrogen peroxide of less than 85 percent does not burn, but it is a strongly oxidising agent, so hydrogen peroxide together with a burning agent causes a serious danger of burning or explosion. Hydrogen peroxide over 85% burns, as it is decomposing, with a blue flame, so its decomposing reaction differs from that of hydrogen peroxide solutions weaker than that.

When decomposing, hydrogen peroxide turns into water and oxygen.

$$2H_2O_2 \rightarrow 2H_2O + O_2.$$

Hydrogen peroxide is unstable and decomposes by itself, but the reaction is extremely slow. The reaction may be accelerated by the use of a catalyst (such as manganese dioxide). In hydrogen peroxide, the oxidation number of oxygen is −I, in decomposition products 0 ($O_2$) and −II ($H_2O$). So, a disproportionation takes place in the reaction, with the oxidation number both increasing and decreasing.

The capability of bleaching and disinfecting of hydrogen peroxide is based on a very reactive free oxygen atom formed in the decomposition process.

Uses

Hydrogen oxide has been used as the oxidant of the fuel used for carrier rockets.

Industrial uses of hydrogen peroxide include bleaching of pulp and textiles and as a disinfectant in medicine and food industries. The hydrogen peroxide used in the industry usually has 35 or 50 percent of hydrogen peroxide, but other concentrations are available as well. For disinfection, hydrogen peroxide of 100 percent may also be used.

Hydrogen peroxide of a low (less than 5 percent) concentration is used in cosmetics, such as hair bleaching, and for example as a cleaning solution of contact lenses, and in disinfecting wounds. The capability of disinfection is based on decomposition of hydrogen peroxide blood acting as the catalyst. The oxygen being released kills bacteria.

Hydrogen peroxide is used rather extensively these days, because its potential release into the air or nature elsewhere only causes short-term harm. Having been released, it decomposes relatively quickly into water and oxygen and does not therefore cause long-term problems for the environment or population.

In Wikipedia, SAILCLOTH, various fibres are listed, the fibres of sailcloth are very suitable for the raw material of the evaporation member.
https://en.wikipedia.org/wiki/Sailcloth Sailcloth covers a wide variety of materials from natural fibres such as linen, hemp or cotton in various types of sailcloth to synthetic fibres including nylon, polyester, aramids, and carbon fibres in a number of woven, spun, and cast textiles.

1 History
    1.1 Western traditions
    1.2 Other traditions
2 Modern fibres
    2.1 Nylon
    2.2 Polyester (PET)
    2.3 PEN fibre (Pentex)
    2.4 Kevlar
    2.5 Technora
    2.6 Twaron
    2.7 Spektri
    2.8 Dyneema
    2.9 Certran
    2.10 Zylon (PBO)
    2.11 Vectran
    2.12 Carbon fibre https://fi.wikipedia.org/wiki/Alumiinioksidi Aluminium oxide, or alumina, ($Al_2O_3$), is an oxide of aluminium. The compound is used in large quantities when aluminium metal is manufactured by the Hall-Héroult method, as additives and fillers on various products and as a catalyst. Aluminium oxide occurs naturally in pure α-aluminium oxide in corundum. Aluminium oxide is industrially produced by the Bayer process. In 2015, approximately 115 million tons of aluminium oxide were produced worldwide.

Most of the produced aluminium oxide is used for the production of metallic aluminium by the Hall-Héroult method. In the method, cryolite is added in aluminium oxide. The mixture of aluminium oxide and cryolite is melted in industrial scale at the temperature of 940 to 980° C., and aluminium is produced by electrolyzing the melt whereby aluminium is reduced by a cathode.

Aluminium oxide is used as additives in paints, in the paper industry, manufacture of glass, as an abrasive due to its hardness, as a catalyst in desulphuration operations and as a carrier of catalysts, in the manufacture of artificial corumdum, ruby, and saphire, in the manufacture of ceramic materials, in TLC plates, as dehumidifiers of hydrocarbons and in the cleaning of chemicals, as a coating for laboratory ovens, and in the electronics industry.

Evaporator material pressed of aluminium oxide. It is capable of pressing into shaped.

LIST OF FIGURES

Figure 2:
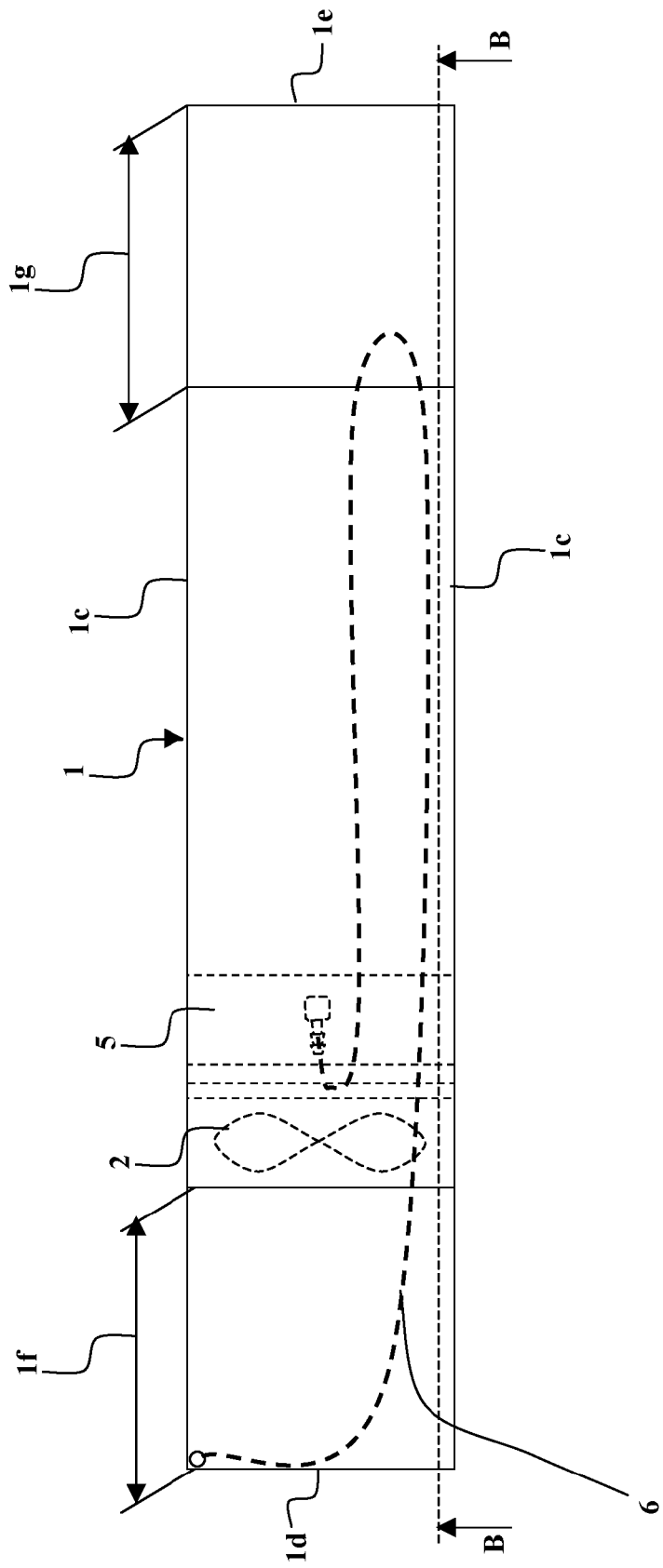
Figure 6:
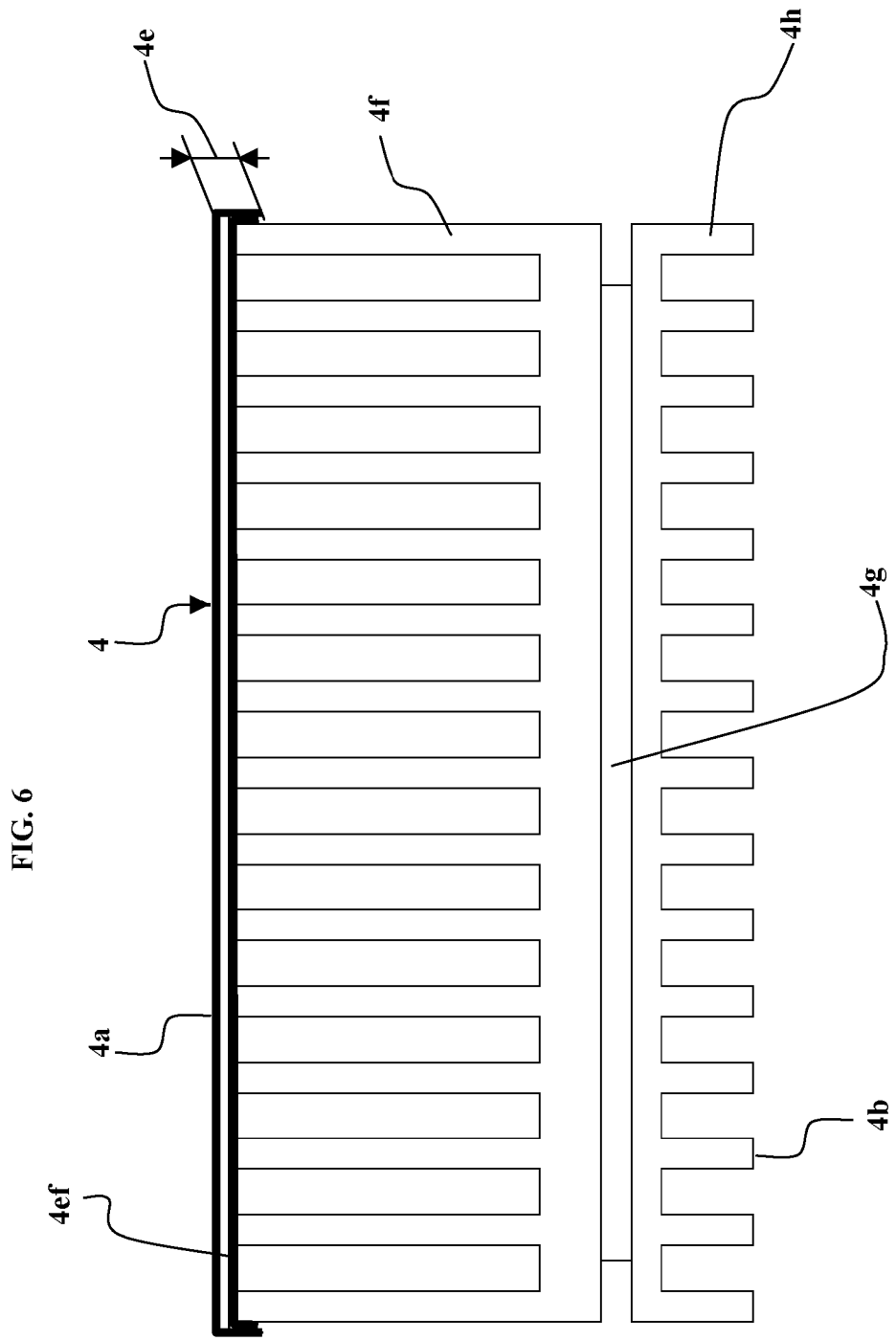
Figure 7:
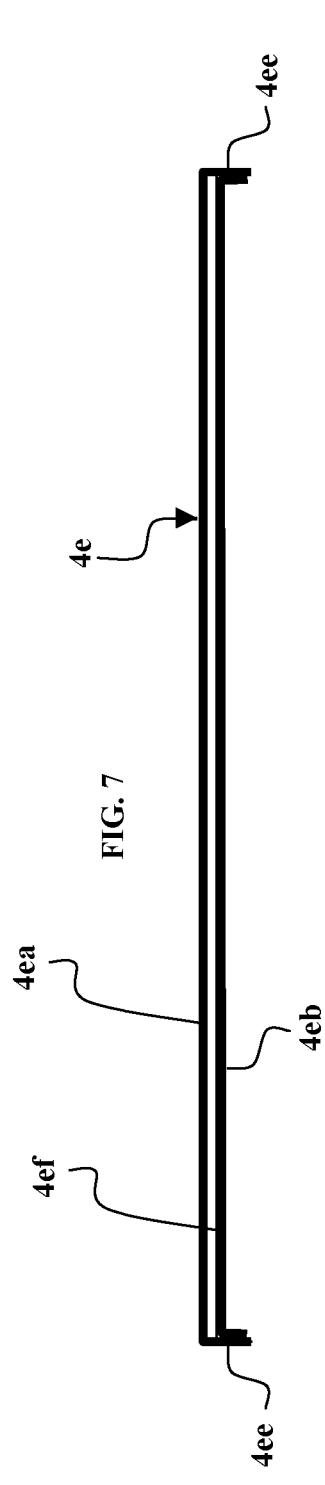
Figure 8:
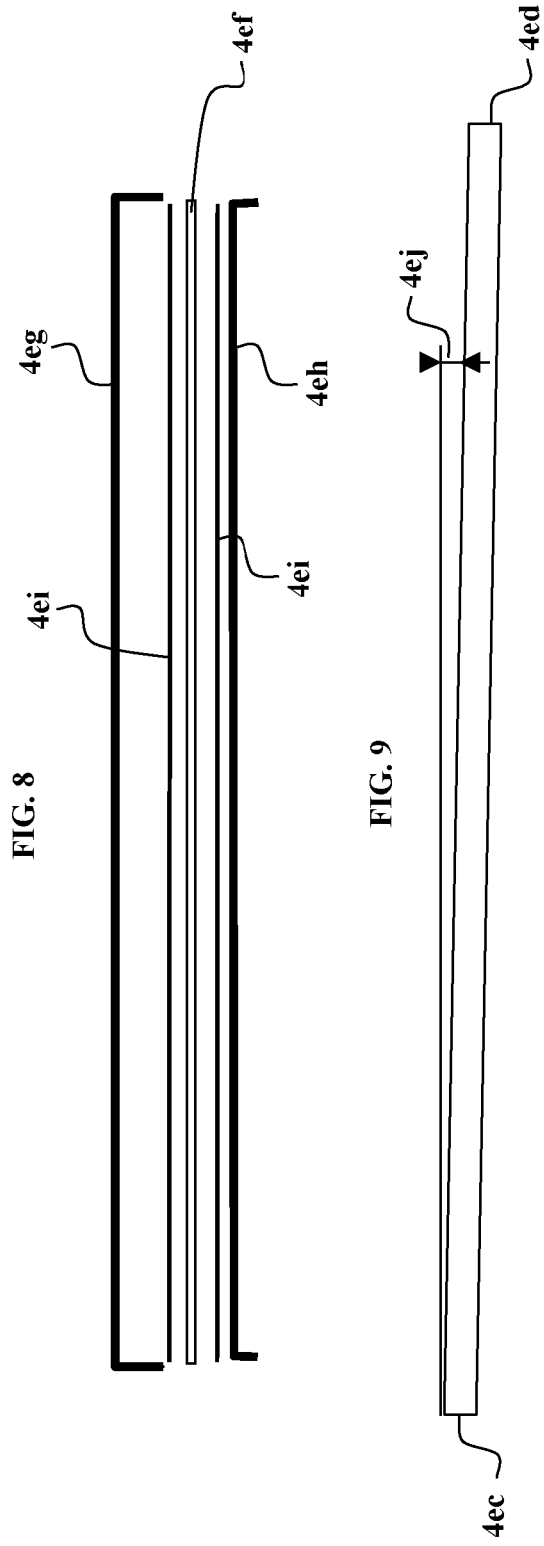
Figure 9:
Figure 10:
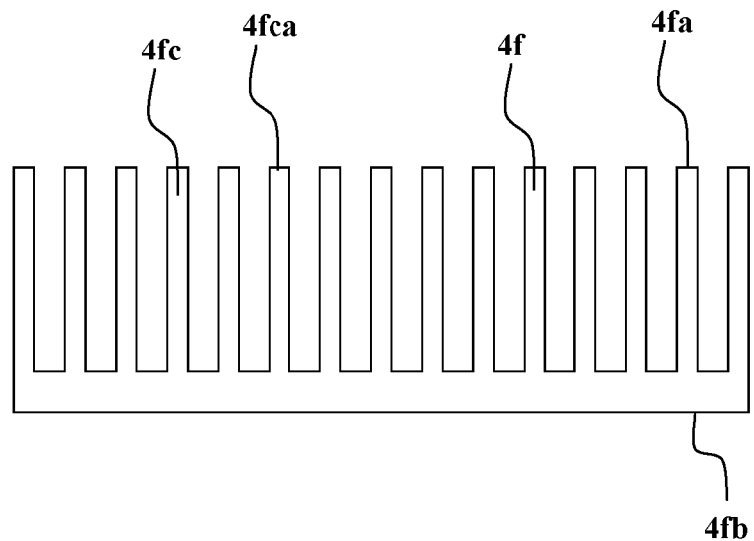
Figure 11:
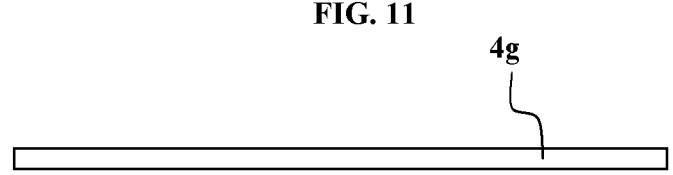
Figure 12:
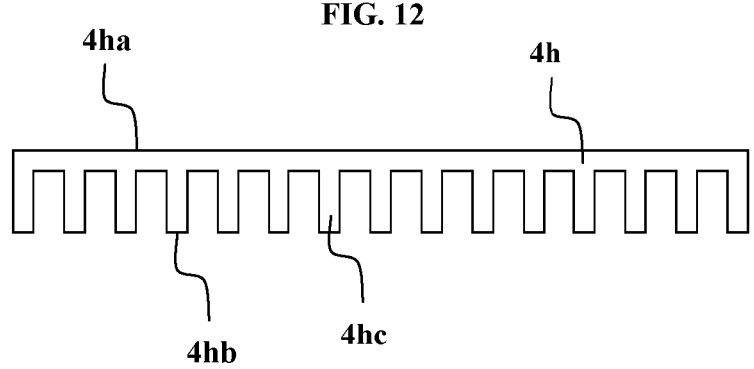
Figure 13:
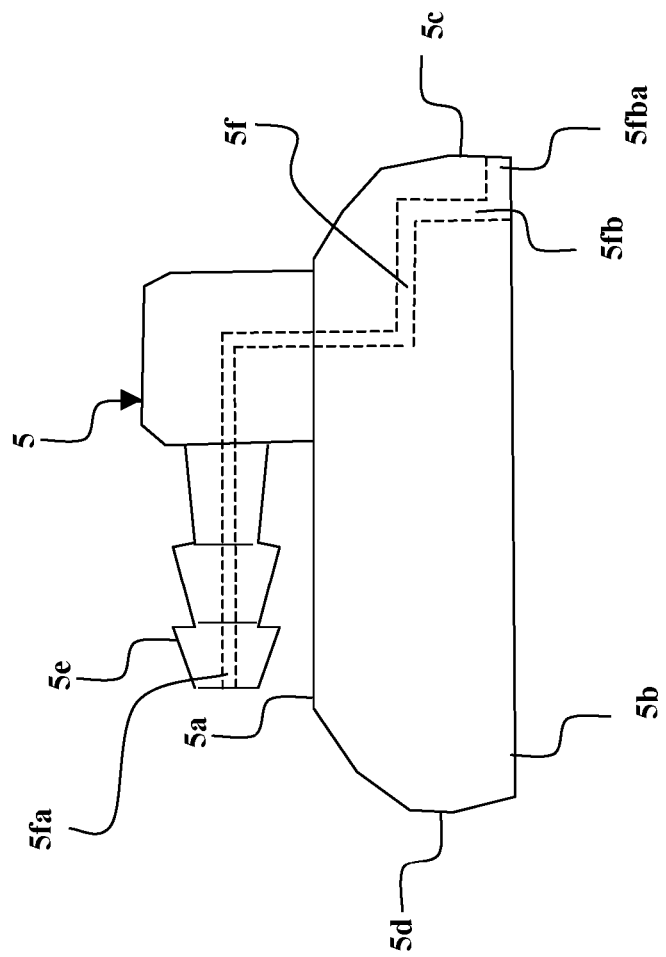
Figure 14:
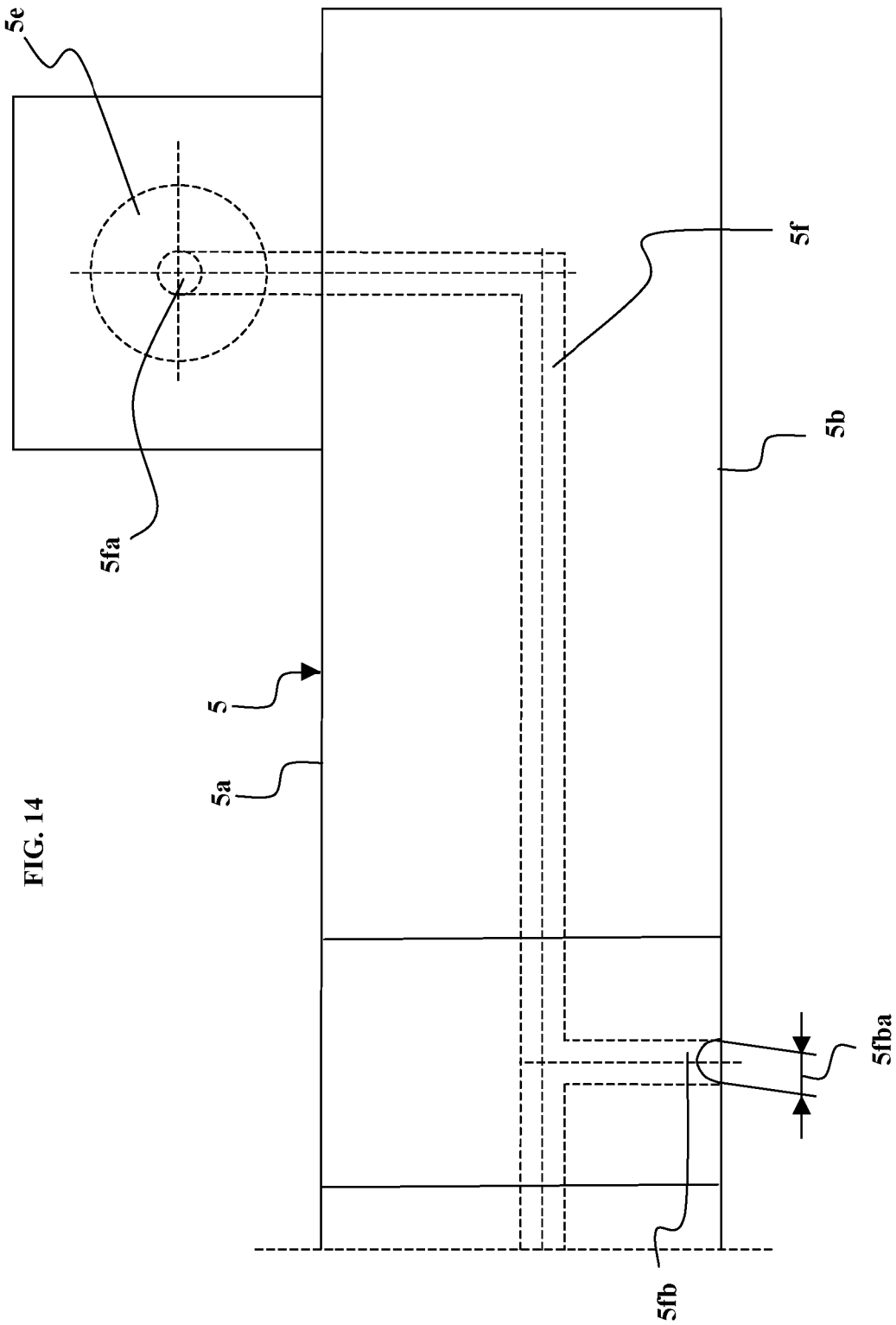
Figure 15:
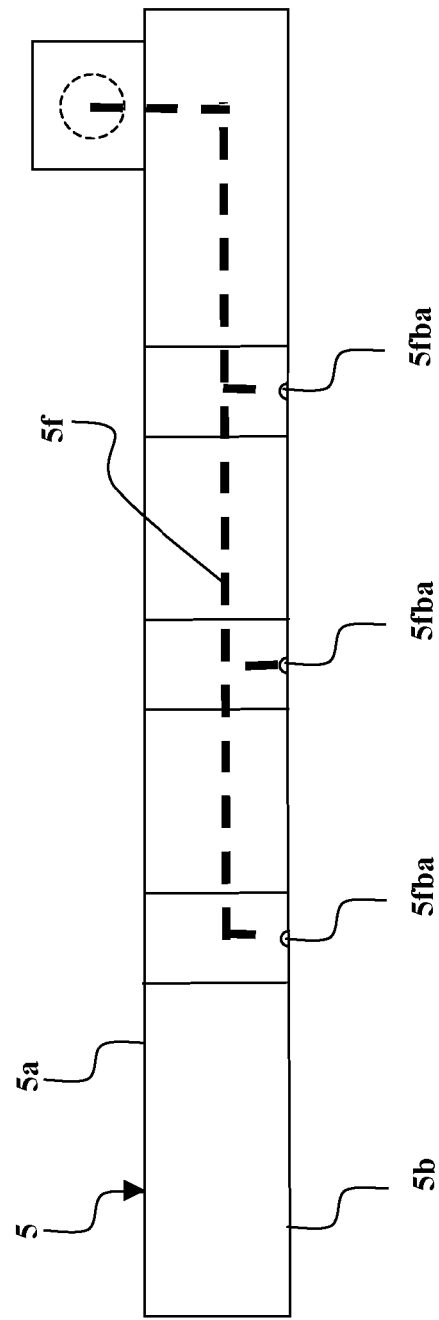
Figure 16:
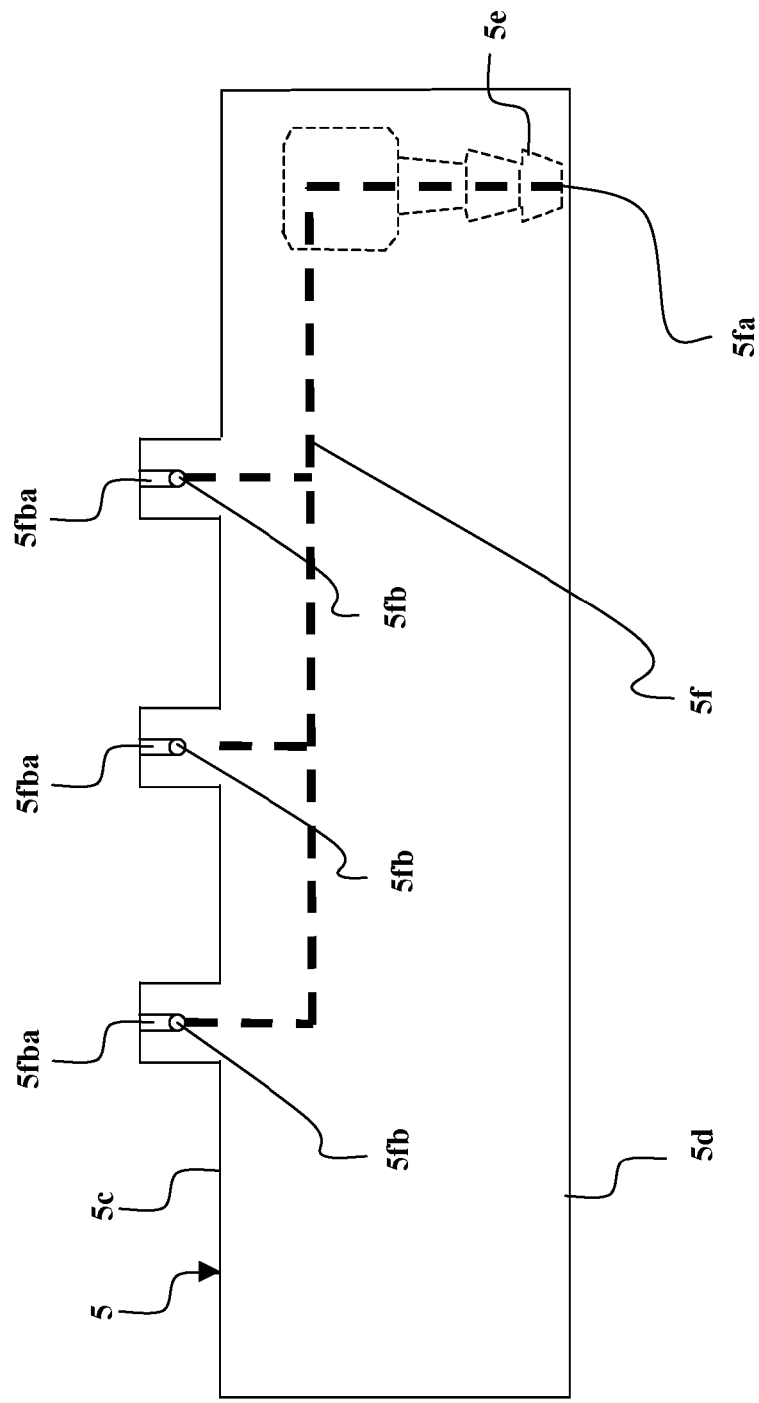
Figure 17:
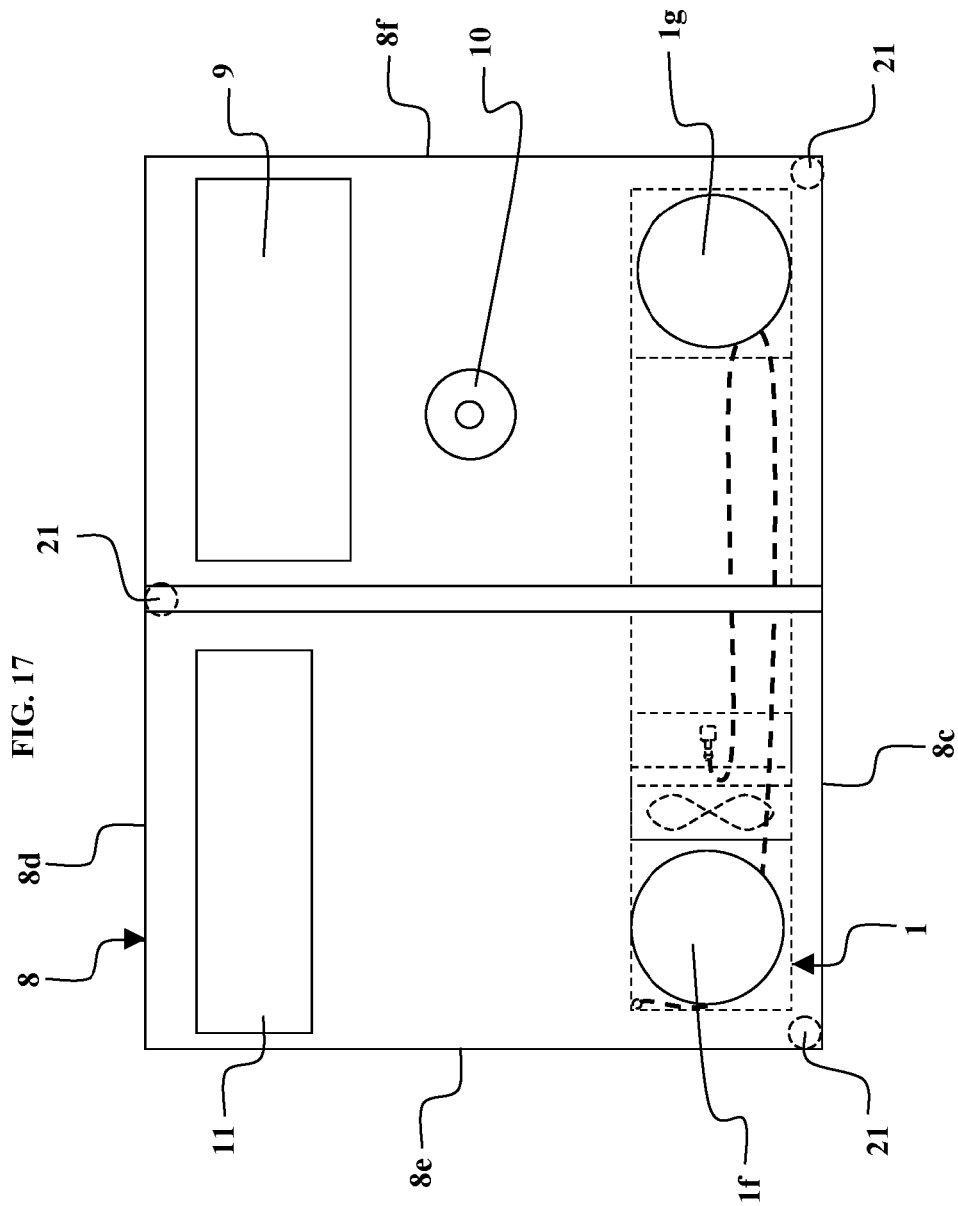
Figure 18:
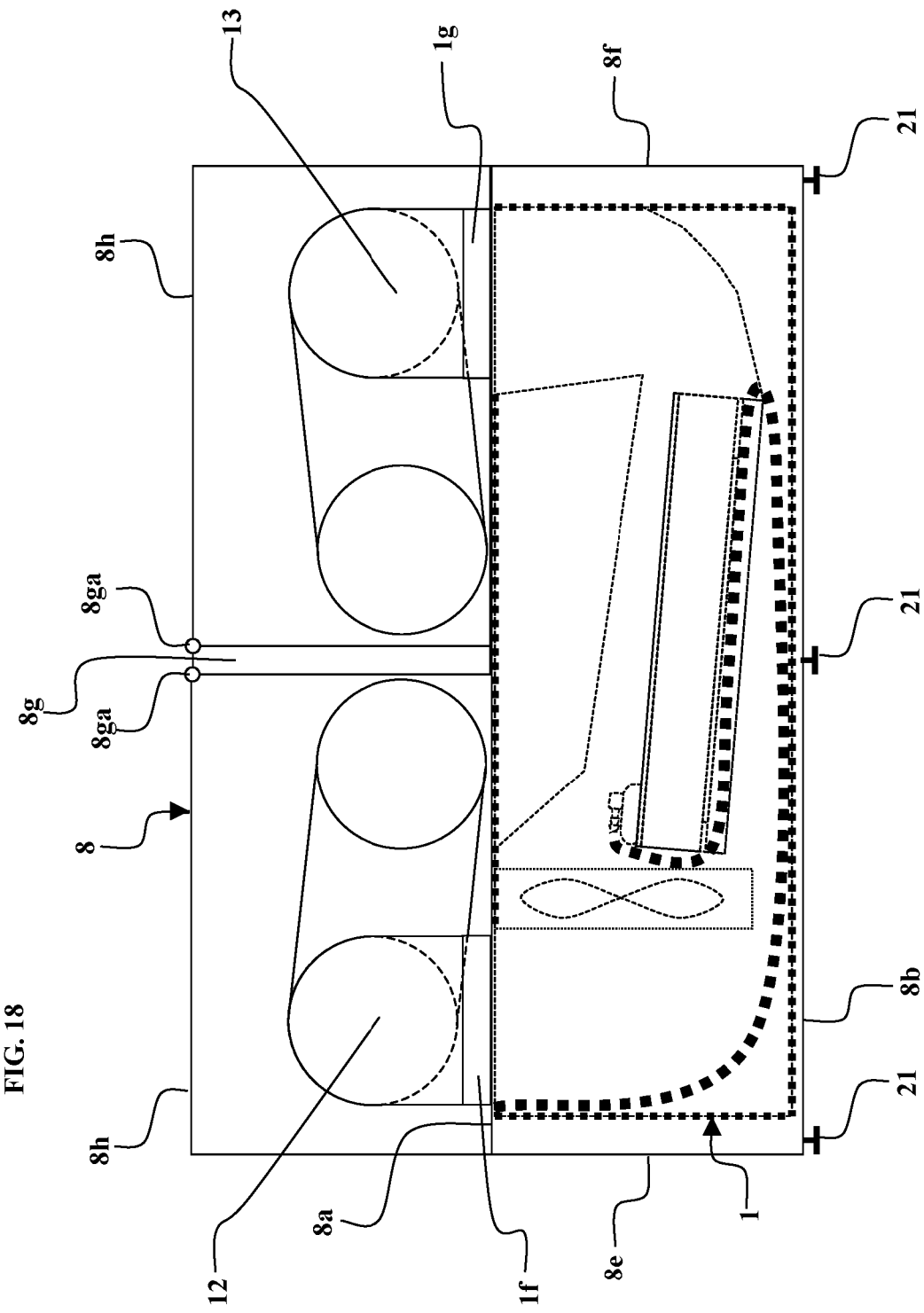
Figure 19:
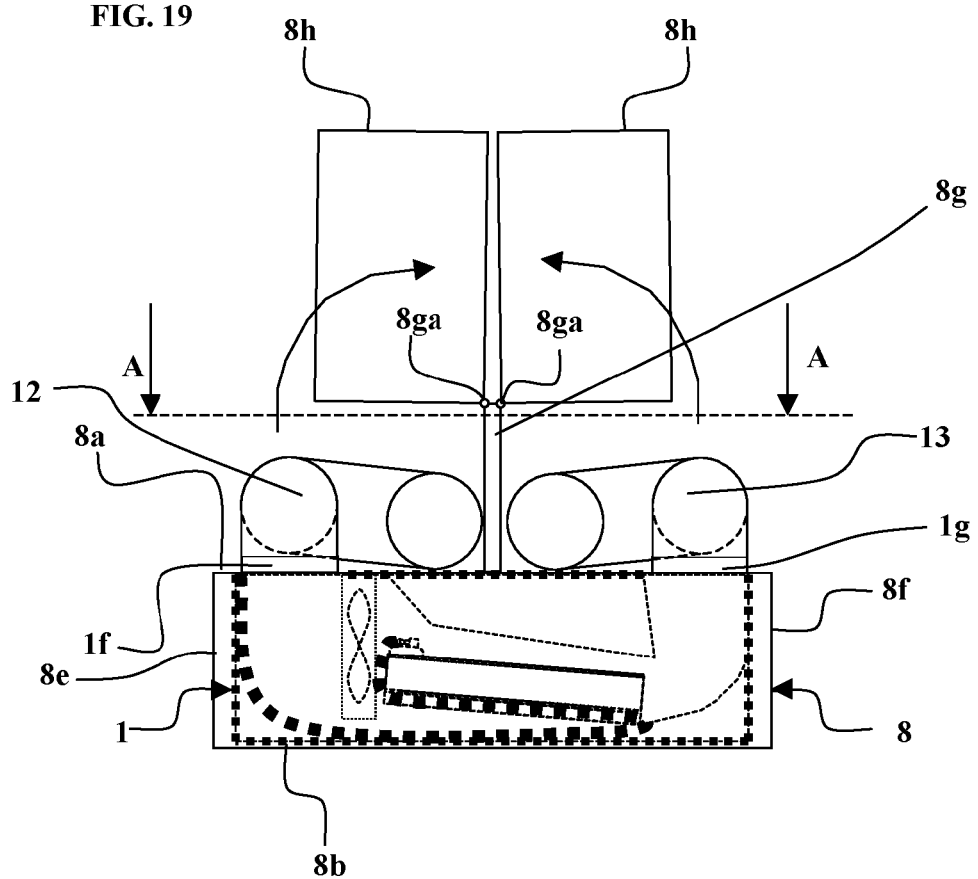
Figure 20:
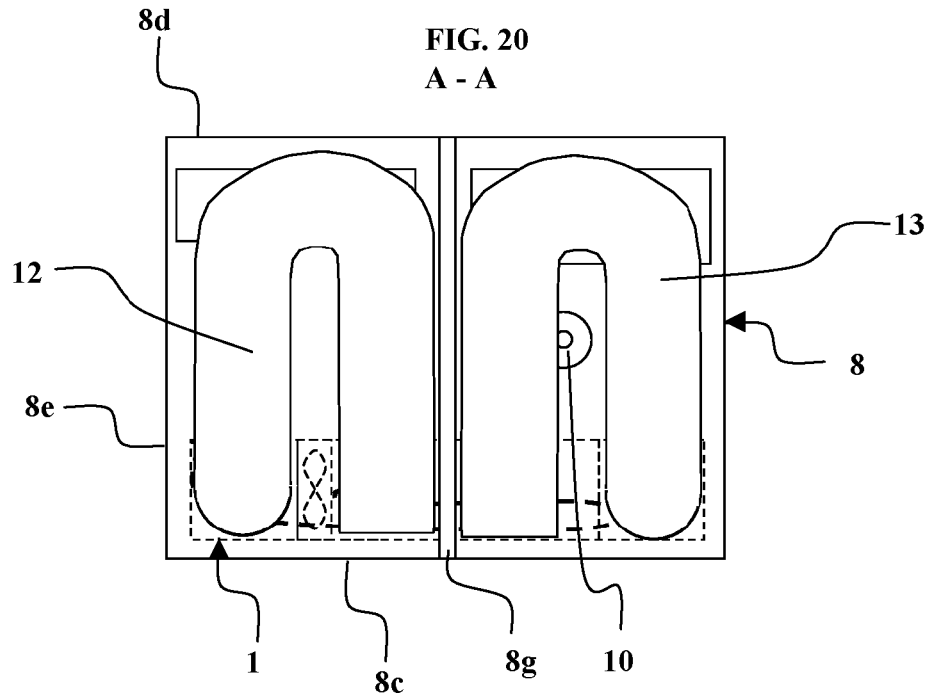
Figure 21:
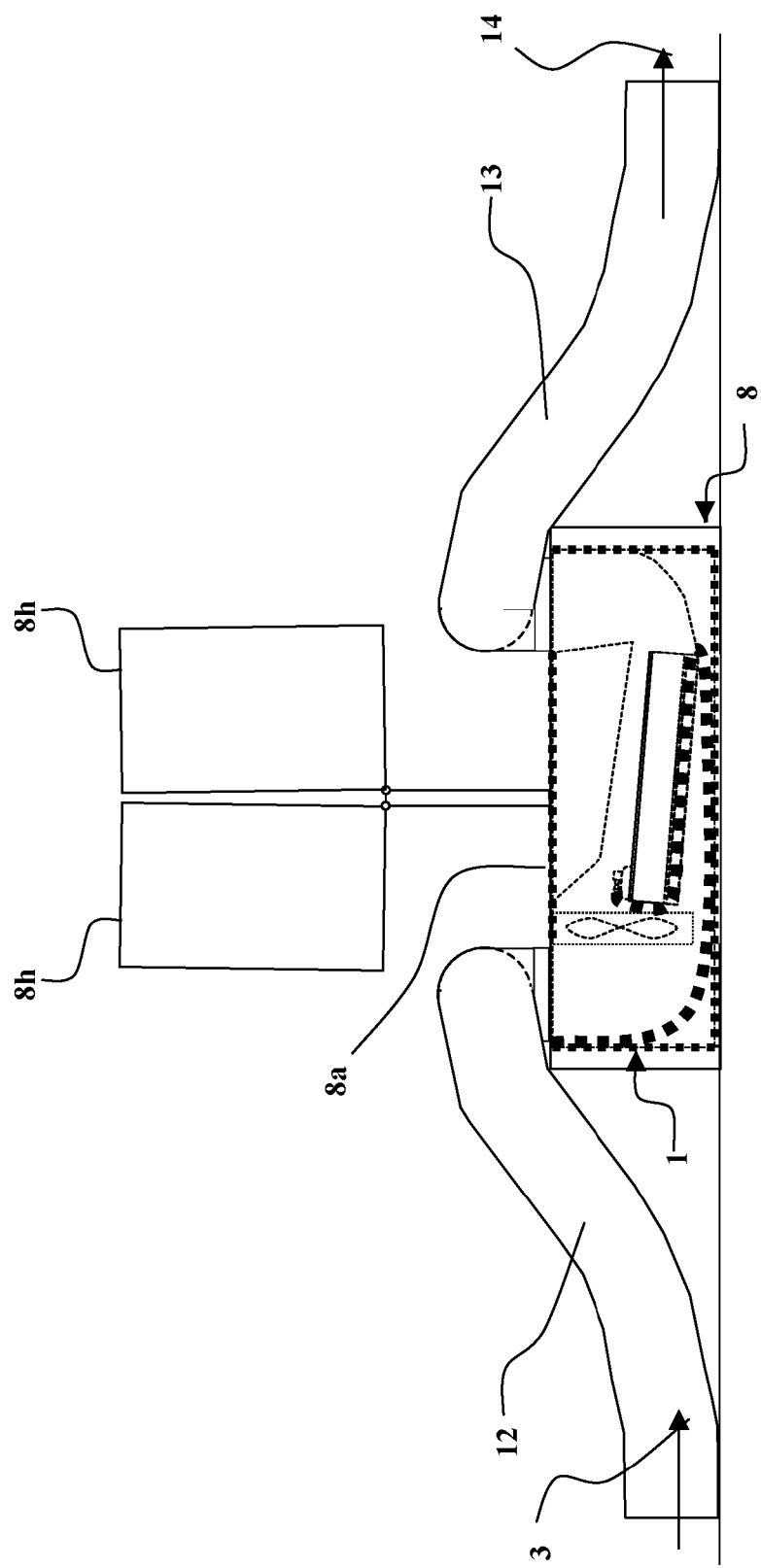
Figure 22:
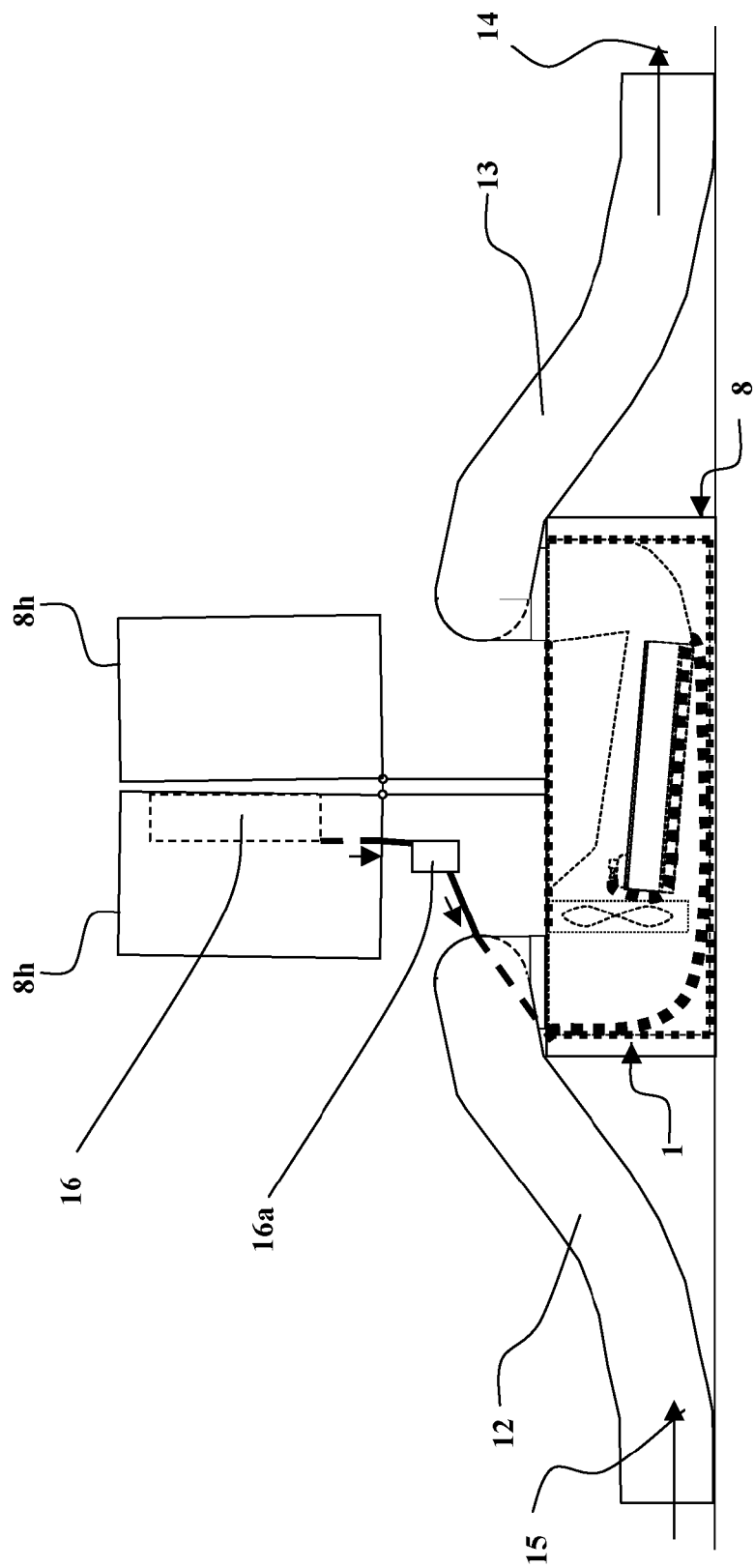
Figure 23:
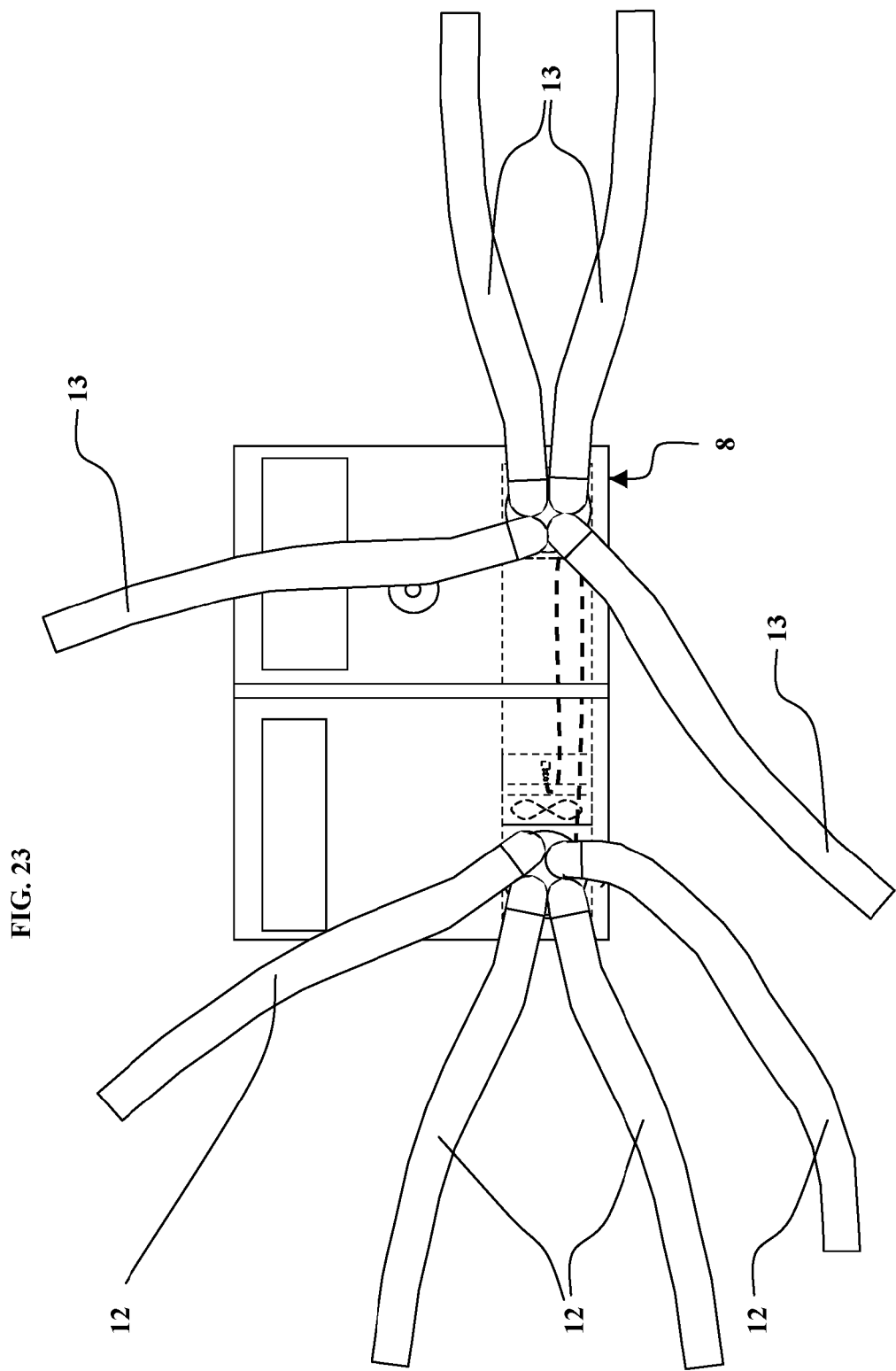
Figure 24:
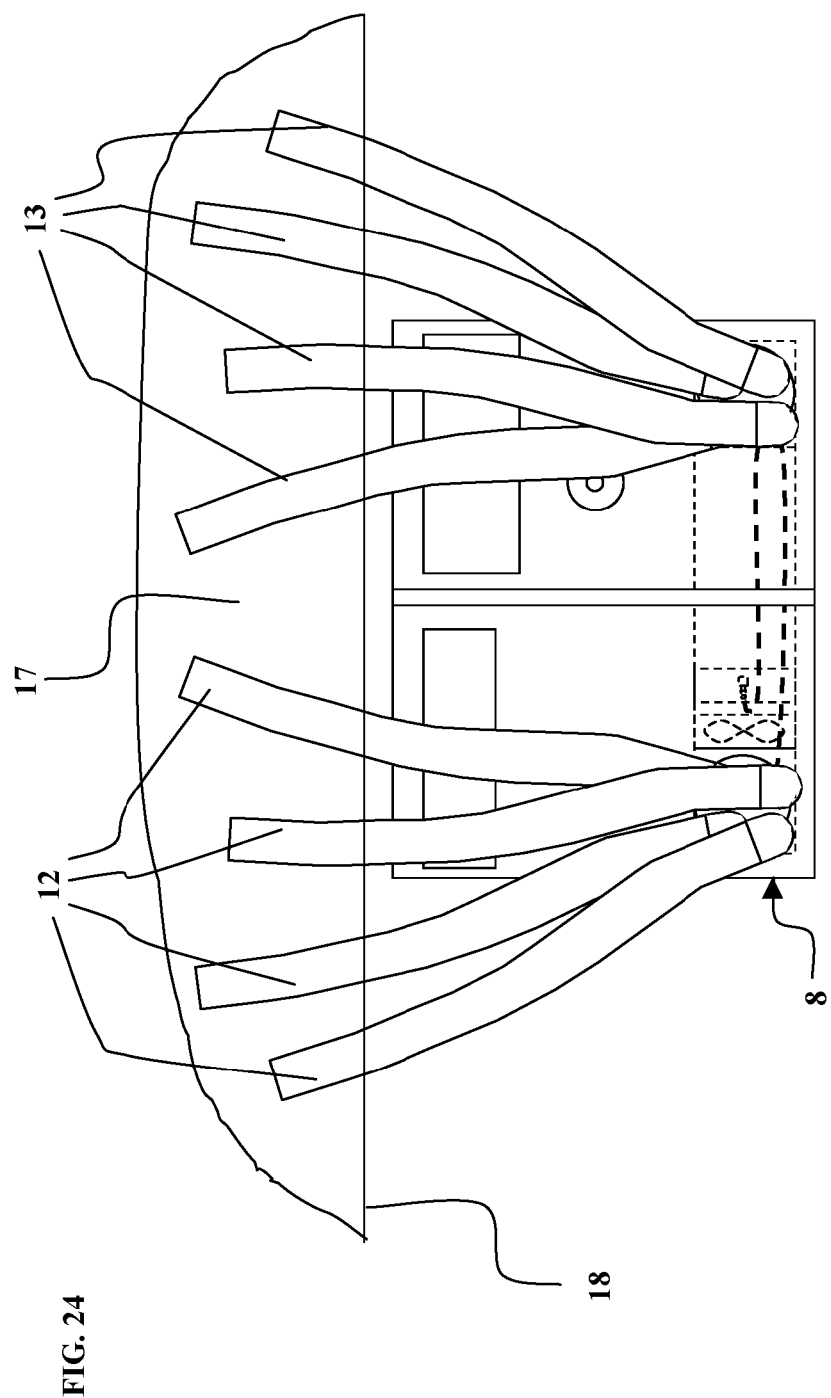
Figure 25:
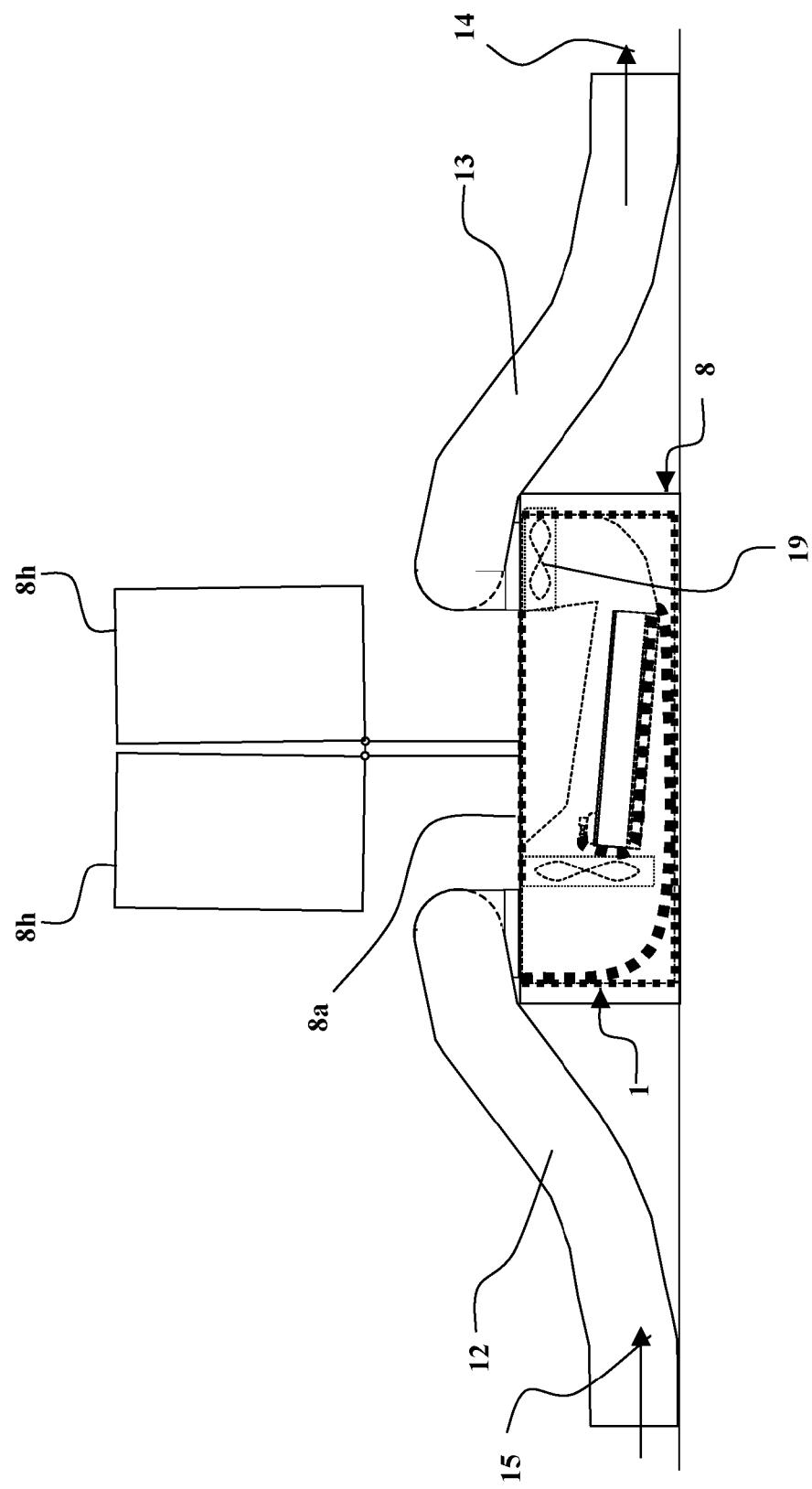
Figure 26:
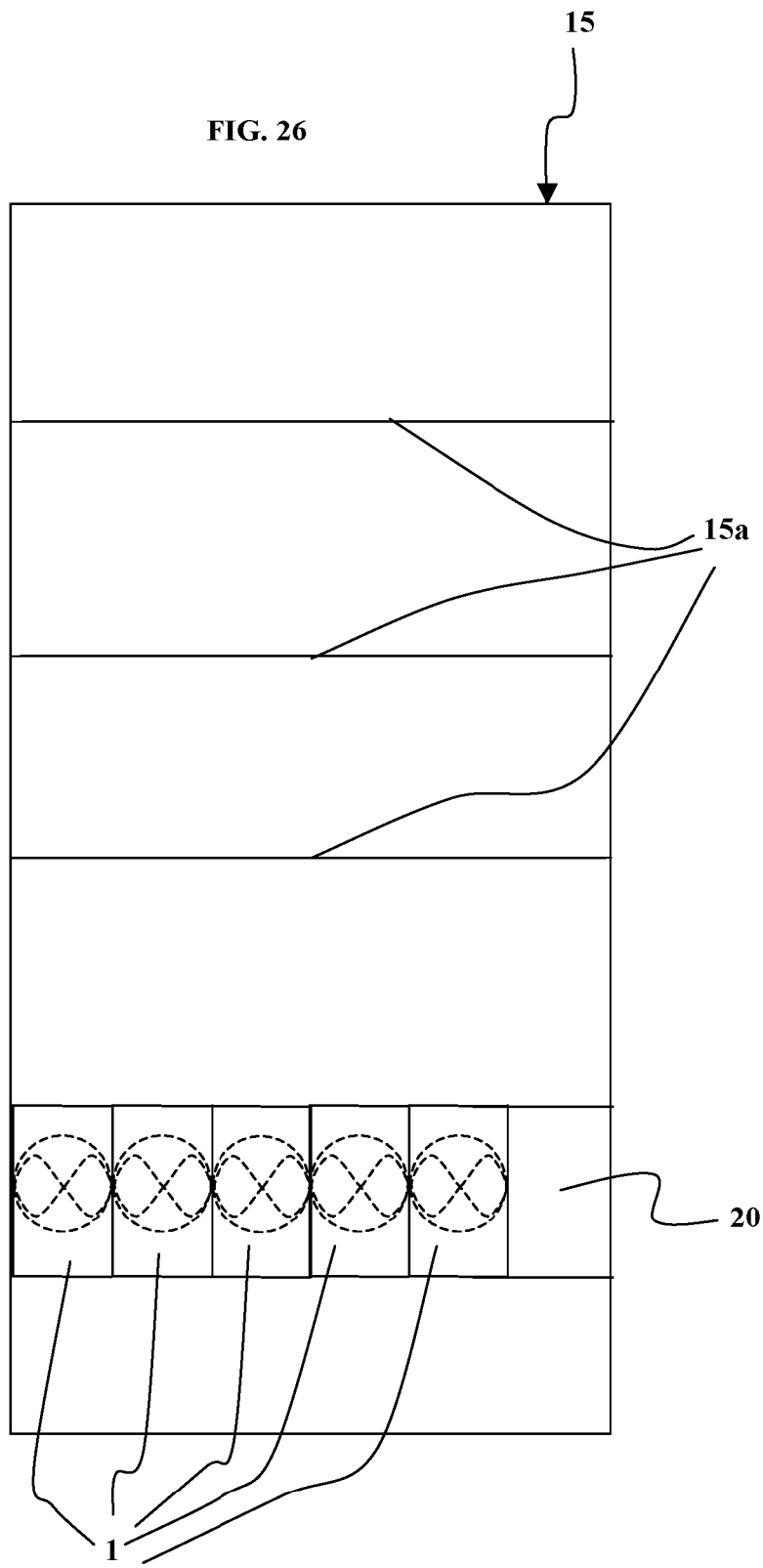
Figure 27:
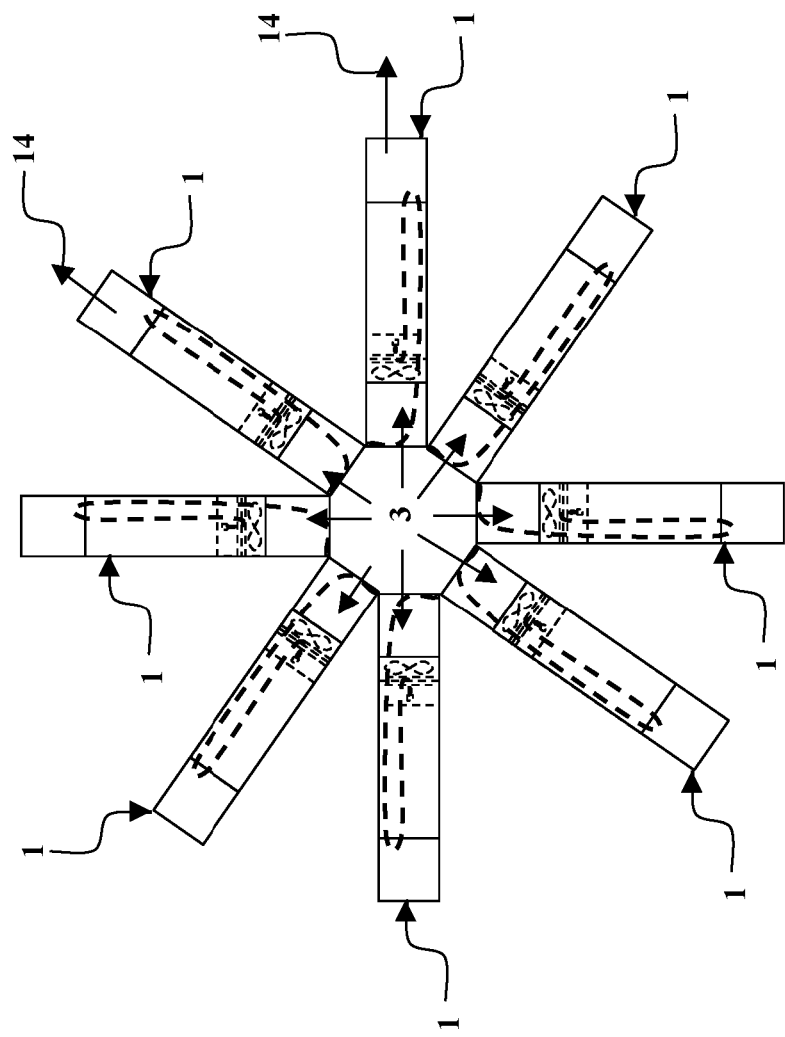

In the following the invention is explained in detail with reference to the accompanying figures, in which FIG. 1 is a sectional perpendicular side view of a disinfection device body according to the invented disinfection method, FIG. 2 is a perpendicular view from the top of the disinfection device body of FIG. 1, FIG. 3 is a perpendicular side view of warming/heating device inside the disinfection device body of FIGS. 1 and 2, FIG. 4 is a is a perpendicular top view of the warming/heating device of FIG. 3, FIG. 5 is a perpendicular end view of the warming/heating device of FIGS. 3 and 4, FIG. 6 is an enlarged perpendicular end view of the warming/heating device of FIG. 5, FIG. 7 is a perpendicular end view of an assembled evaporation member of the warming/heating device of FIG. 6, FIG. 8 is an exploded perpendicular end view of the evaporation member of FIG. 7, FIG. 9 is perpendicular side view of the evaporation member of FIGS. 7 and 8 at a skew angle, where the evaporation member is installed to the disinfection device body, to the left end of FIG. 9 at the top side, there will be a draining device, FIG. 10 is a perpendicular end view of a warming member of the warming/heating device of FIGS. 5 and 6, FIG. 11 is a perpendicular end view of a warmer of the warming/heating device of FIGS. 5 and 6, FIG. 12 is a perpendicular end view of a cooler of the warming/heating device of FIGS. 5 and 6, FIG. 13 is a perpendicular side view of a draining device of hydrogen peroxide, inside the disinfection device body of FIGS. 1 and 2, the hydrogen peroxide liquid drains from underside the draining device through draining channels opening on the right side of the Figure, FIG. 14 is a perpendicular detailed view form the draining direction of the draining device of FIG. 13, FIG. 15 is a perpendicular view from the draining direction of the draining device of FIGS. 13 and 14 as seen perpendicularly from the draining direction, FIG. 16 is a perpendicular view from underside of the draining device of FIGS. 13, 14 and 15, FIG. 17 is a perpendicular view from the top of the disinfection device body of FIGS. 1 and 2, placed in a usage space, FIG. 18 is a perpendicular front view of the disinfection device body of FIG. 17, placed in a usage space, the usage space closed, in the usage space, on the left, a suction channel/suction pipe is drawn as bent into a transport position, and on the right, a blow channel/blow pipe bent into a transport position, FIG. 19 is a perpendicular front view of the disinfection device body of FIG. 18, placed in a usage space, the usage space opened, FIG. 20 is a perpendicular top view of the disinfection device body of FIGS. 18 and 19, placed in a usage space, FIG. 21 shows the disinfection device body of FIGS. 18, 19, and 20 placed in a usage space, the usage space opened, in the usage space, on the left, a suction channel/suction pipe is drawn opened into use position/cleaning position, and on the right, a blow channel/blow pipe opened into a use position/cleaning position, as seen perpendicularly from the front, FIG. 22 is a perpendicular front view of the disinfection device body of FIG. 21 placed in a usage space, the usage space opened, in the usage space, on the left, is drawn a hydrogen peroxide tank suspended from the cover of the usage space, from where hydrogen peroxide drains under gravity to the draining device, FIG. 23 is a view of a second disinfection device according to the invention, a disinfection device body placed in a usage space, as seen perpendicularly from the top, the usage space opened, in the usage space, on the left, a suction channel network/suction pipes are drawn opened into use position/cleaning position, and on the right, a blow channel system/blow pipes opened into a use position/cleaning position, FIG. 24 is a view of the disinfection device body of FIG. 23 placed in a usage space, as seen perpendicularly from the top, the usage space opened, in the usage space, on the left, a suction channel network/suction pipes are drawn opened into use position/cleaning position, and on the right, a blow channel network/blow pipes opened into a use/cleaning position, the suction channels/suction pipes and blow channels/blow pipes pass through a gas tight partition wall to the space to be cleaned, FIG. 25 is a view of a third disinfection device of the invention, the disinfection device body placed in a usage space, as seen perpendicularly from the front, the usage space opened, in the usage space, on the left, a suction channel/suction pipe is drawn opened into use position/cleaning position, and on the right, a blow channel/blow pipe opened into a use/cleaning position, the usage space has a pressure blower to blow hydrogen peroxide gas to the blow channels/blow pipes, FIG. 26 is a view of a fourth disinfection device of the invention, disinfection device bodies placed in a disinfection cabinet, as seen perpendicularly from the front, in FIG. 26 one place is missing a disinfection device body, the Figure illustrates that desired number of disinfection device bodies may be placed in a disinfection cabinet, whereby the disinfection power of the disinfection cabinet is adjustable, FIG. 27 is a perpendicular view from the top of a fifth disinfection device of the invention, disinfection device bodies placed in a star shape.

Figure 28:
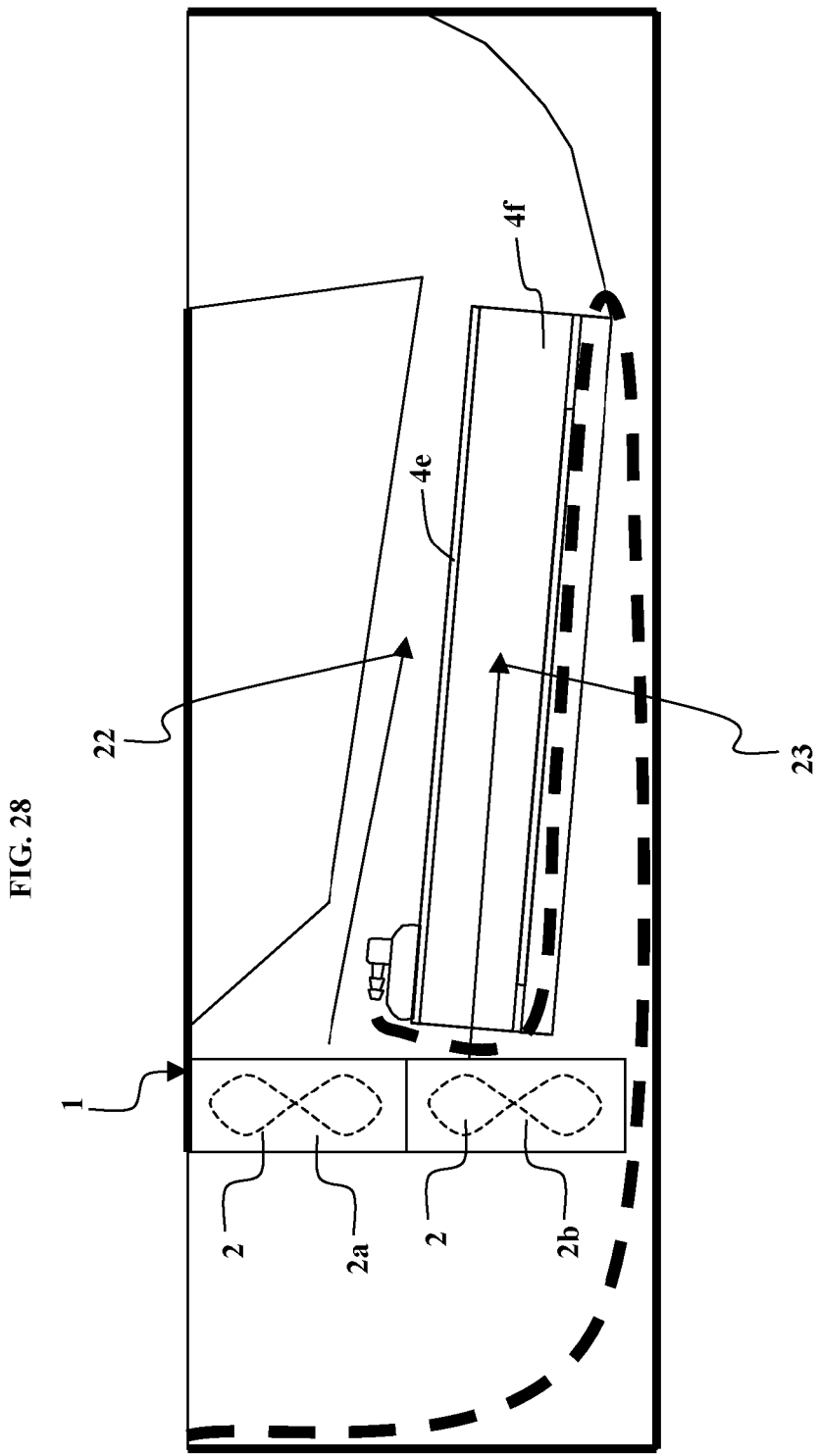
Figure 29:
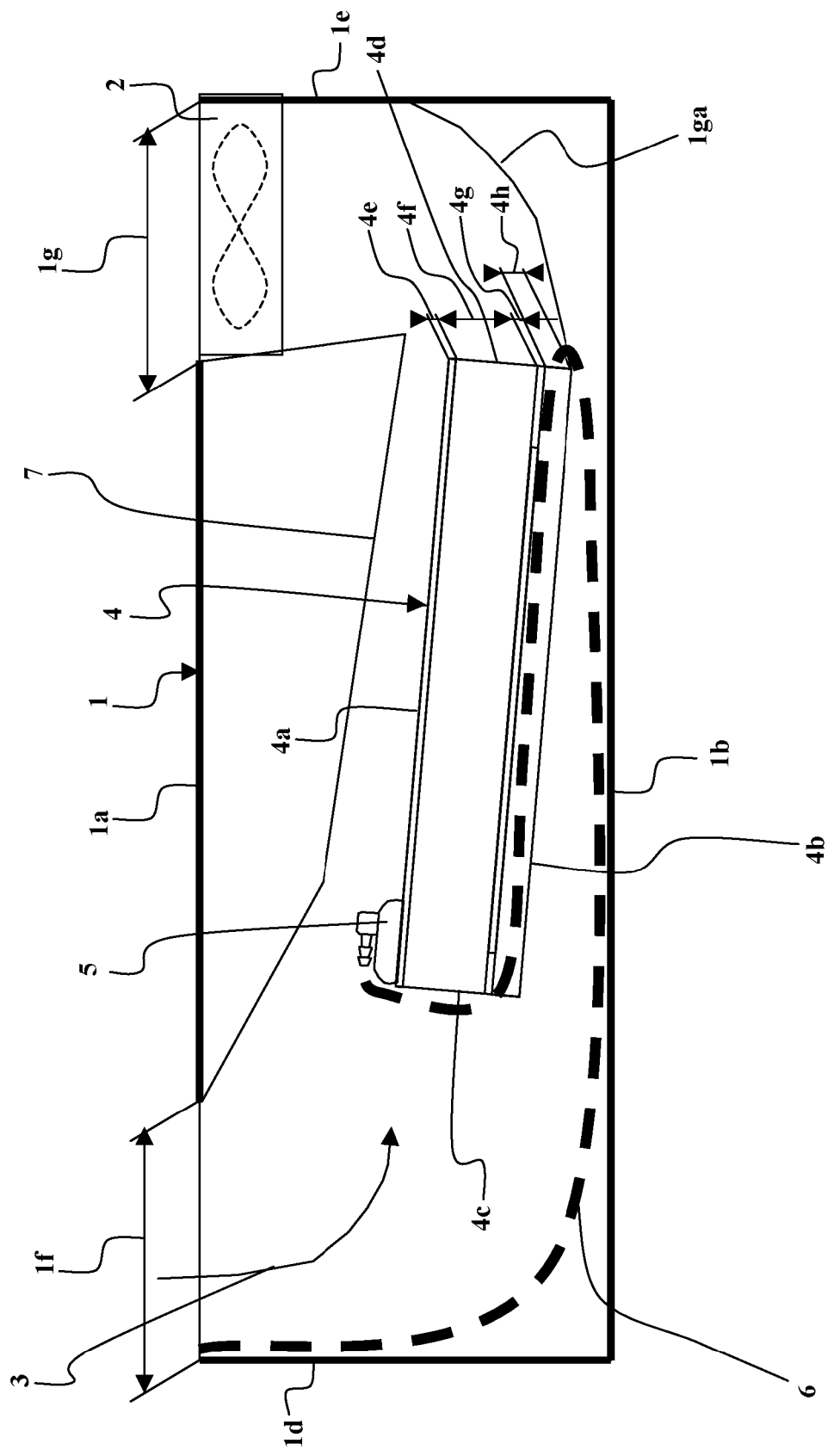
Figure 30:
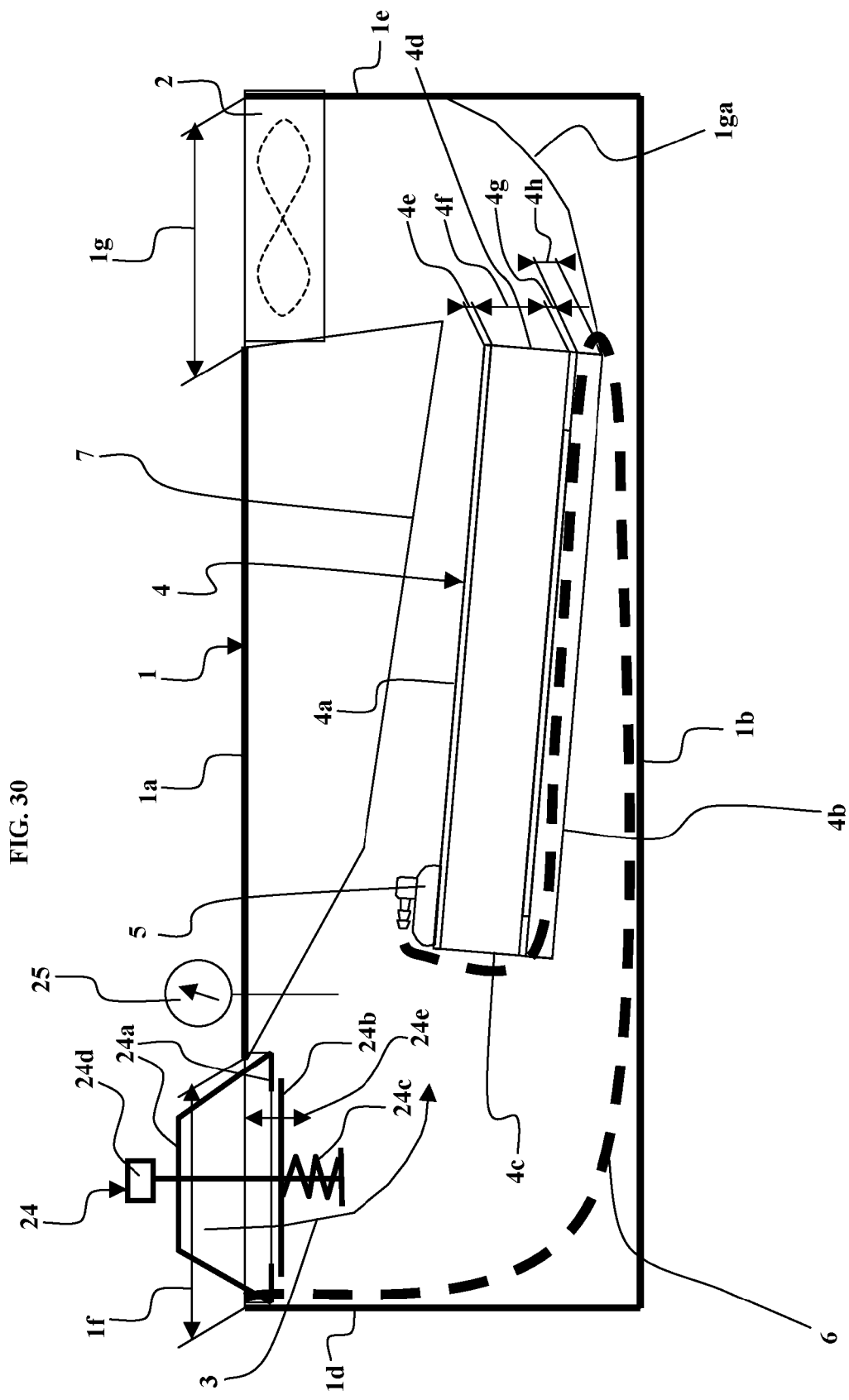

FIG. 28 is a perpendicular side view of a sixth disinfection device of the invention, the disinfection device body in cross section, there are two successive blowers inside the disinfection device body, FIG. 29 is a perpendicular side view of a seventh disinfection device of the invention, disinfection device body in cross section, there is a blower inside the disinfection device body, placed at the air discharge end whereby the blower generates a vacuum to the disinfection device body, FIG. 30 is a perpendicular side view of an eighth disinfection device of the invention, disinfection device body in cross section, there is a blower inside the disinfection device body, placed at the air discharge end whereby the blower generates a vacuum to the disinfection device body, there is an adjustable inward relief valve at the suction end of the body.

DETAILED DESCRIPTION OF THE INVENTION

The invention shown in the accompanying figures and the associated parts are not shown in scale but the figures are schematic, illustrating the structure and operation of the preferred embodiment of the invention and its parts in principle.

The parts and points of the disinfection device, shown in the figures.

In the figures, the disinfection device body 1 is a closed, rectangular box made of metal, preferably stainless steel, on the top side 1a of which at the suction end 1d there is one or more suction opening/suction passages 1f, from which suction opening/suction passage 1f air/gas may enter inside the disinfection device body 1, said air/gas being used inside the disinfection device body 1 to vaporize hydrogen peroxide ($H_2O_2$). On the top side 1a of the disinfection device body 1 at the blowing end 1e there is one or more blowing opening/blowing passages 1g from which blowing opening/blowing passage 1g hydrogen peroxide ($H_2O_2$) hydrogen peroxide gas 14 may access the target(s) to be cleaned directly or through a desired pipe etc. passage/channel to one or more desired target(s). Unlike in the figures, the suction opening/suction passage 1f and blowing opening/blowing passage 1g may be located at an end/ends, underside, or side of the disinfection device body 1, the location may be freely chosen as needed because the blower 2 carries out the circulation of air or gas and air mixture. One or more suction channel/suction pipes 12 and blowing channel/blowing pipe 13 may be fastened as known the best rotatably, as shown in FIGS. 18, 19, 20, 21, 22, 23, 24 and 25, to the suction opening/suction passage 1f and blowing opening/blowing passage 1g.

The disinfection device body 1 has a top side 1a, underside 1b, side 1c, suction end 1d, blowing end 1e, suction opening/suction passage 1f, blowing opening/blowing passage 1g.

A blowing guide 1ga is formed in the figures of bent sheet metal, preferably stainless, fixed inside the disinfection device body 1 at the blowing end 1e.

One or more blowers 2 to blow clean air or to circulate air to be cleaned. The blower/blowers 2 suck suction air 3 inside the disinfection device body 1 through one or more suction openings/suction passages 1f at the suction end 1d.

The blower 2 is the best known axial blower, centrifugal blower or a similar device moving gas/air, which sucks gas/air in the direction shown by the arrow 3. Most preferably filtered air, the filter/cleaner known from the construction industry is not shown in the figures. Suction air 3, which suction air 3 may be air, nitrogen, argon, or a mixture of the aforementioned. The blower/blowers 2 blow suction air 3 to the draining end 4c of the hydrogen peroxide of the warming/heating device 4, being almost at horizontal plane as seen from the side.

To blow suction air 3, an air guide/pipe system may also be used to bring in air for the warming/heating device 4. With the same technology, a single large blower may be used, by means of which suction air 3 is blown to a plurality of warming/heating devices 4. for example in the structure solution of FIG. 27 one large blower is used to blow suction air 3 to eight disinfection device bodies 1 and the warming/heating devices 4 therein.

The warming/heating device 4 has a top side 4a, underside 4b, draining end 4c, gas discharge end 4d, and side 4e.

The evaporation member 4e is the topmost part of the warming/heating device 4, on the top surface of which to the draining end 4c hydrogen peroxide is drained from one or more draining devices 5.

The evaporation member 4e is formed of a fibreglass braiding. The evaporation top surface 4ea of the evaporation member 4 is at an evaporation angle 4ej of 1 to 30 degrees as seen from the side so that the evaporation draining end 4ec is higher than the evaporation gas end 4ed whereby hydrogen peroxide drains downhill and is evenly spread on the entire evaporation top surface 4ea following the draining device 5 of the evaporation member 4e.

The evaporation member 4e has an evaporation top surface 4ea, evaporation bottom surface 4eb, evaporation draining end 4ec, evaporation gas end 4ed, evaporation member side 4ee, and fibreglass braiding 4ef.

The fibreglass braiding 4ef is of known crosswise woven fibreglass braiding 4ef, which may also be referred to as a fibreglass mat. The density of the fibreglass braiding 4ef is such that air may pass through the fibreglass braiding, the thickness of the fibreglass braiding 4ef is 0.5 to 3 mm depending on the area of the evaporation member 4e.

In FIG. 4, a top frame 4eg has in the figures a rectangular opening 4ek to the evaporation top surface 4ea, from the area of this opening 4ek hydrogen peroxide may vaporize. The shape of the opening 4ek may differ from the rectangle of the figures, the shape as seen from above may be a cone or oval, or of another known shape.

In the Figures, a bottom frame 4*eh* has a rectangular opening 4*ek*, from the area of this opening 4*ek* the air from the blower 2 get to vaporize hydrogen peroxide from underside.

A net 4*ei* is a net at best made of stainless steel with a mesh size of 2 to 5 mm and wire thickness 0.3 to 1.0 mm, the net 4*ei* shape as seen from above is preferably square. Unlike in the Figures, the fibreglass braiding 4*ef* may be glued by heat-resistant glue to the top frame 4*eg* whereby the bottom frame 4*eh* will not be needed. On top of the fibreglass braiding 4*ef* there is a net 4*ei* which prevents an uncontrollable draining of hydrogen peroxide.

FIG. 8 shows that the net 4*ei* is at the top side and underside of the fibreglass braiding 4*ef* whereby the fibreglass braiding 4*ef* is pressed between the nets 4*ei*, pressed by the top frame 4*eg* and bottom frame 4 *eh*, whereby fastening by glue is not needed. The top frame 4*eg* and bottom frame 4*eh* may be fixed to one another by known rivets, for example, preferably the downward bent sides (in FIGS. 7 and 8) of the bottom frame 4*eg* and bottom frame 4*eh* are doubled to an internal angle of 80 to 89 degrees whereby the top frame 4*eg* and bottom frame 4*eh* adhere to each other on their sides that are bent over by a compression joint connection.

In the figures, the warming member 4*f* is an aluminium piece, equipped with warming top side 4*fa* warming ribs 4*fc*.

The warming member 4*f* has a warming top side 4*fa*, warming underside 4*fb*, warming rib 4*fc* and in it a warming rid end 4*fca*.

In the figures, the warmer 4*g* is a warming plate continuously adjustable by electricity (electric energy), made of known electric elements by a known method, such as electric elements of the kind used in electric stoves, whose temperature may be continuously adjusted, as known.

A cooler 4*h*, the lowest part of the warming/heating device 4, the task of the cooler 4*h* is to manage the temperature of the warmer 4*g* by cooling the warmer 4*g* from the underside. The cooler 4*h* has a cooling top side 4*ha* and a cooling underside 4*hb*. In the figures, the cooler 4*h* is an aluminium piece, equipped with cooling underside 4*hb* cooling ribs 4*hc*. The cooler 4*h* has a cooling top side 4*ha*, a cooling underside 4*hb*, and one or more cooling ribs 4*hc*.

The draining device 5 of hydrogen peroxide is in the figures a piece manufactured by printing it from plastic, which has a draining pipe connector 5*e* and draining channel 5*f* for a draining pipe 6.

The draining device 5 has a draining top side 5*a*, a draining underside 5*b*, a draining side 5*c*, a blower side 5*d*, a draining pipe connector 5*e*.

The draining lower sider 5*b* hydrogen peroxide drains to the evaporation member 4*e* from the draining lower side 5*b*, more specifically to the draining side 5*c*. The draining side 5*c* is the side of the evaporation gas end 4*ed*, that is, the lower side of the evaporation member 4*e*. The blower side 5*d* is the side of the blower 2 side.

The draining channel 5*f* is one or more openings inside the draining device 5, which branches out to a plurality of openings. The draining channel 5*f* starts at one or more draining pipe connectors 5*e* which is an inlet end 5*fa* of hydrogen peroxide and the draining channel 5*f* ends at an outlet draining end 5*fb* of hydrogen peroxide, in which outlet draining end of hydrogen peroxide 5*fb* has one or more draining guides 5*fba* of hydrogen peroxide.

The draining channel 5*f* has an inlet end 5*fa* of hydrogen peroxide and outlet draining end 5*fb* of hydrogen peroxide.

At the hydrogen peroxide outlet draining end 5*fb* there is a hydrogen peroxide draining guide 5*fba*. In the Figures, the hydrogen peroxide draining guide 5*fba* is a groove parallel to the draining bottom side 5*b*, along which hydrogen peroxide drains and spreads on the evaporation top side 4*ea* of the evaporation member 4*e*. In the Figures, there are three hydrogen peroxide draining guides 5*fba* but unlike in the Figures, there may be one or more pieces of them depending on the width of the warming/heating device 4, that is, the width of the evaporation surface of hydrogen peroxide.

The draining member 6 of hydrogen peroxide is at best a pipe and hose combination so that the starting end of the draining member is of a flexible transparent hose e.g. known from infusion bags of different kind of substances used in hospital technology, and the finishing end of the draining member 6 inside the disinfection device body 1 is of a known metal pipe, such as aluminium pipe, which in accordance with FIGS. 1 and 2, among others, is bent in between the ribs of the warming member 4*f* and/or the cooler 4*h*, whereby hydrogen peroxide is pre-warmed as it runs inside the metal pipe towards the draining device 5.

An air guide 7 which directs the airflow from the blower 2 to the fibreglass braiding 4*ef* whereby the hydrogen peroxide liquid draining/flowing onto the fibreglass braiding 4*ef* from the draining device 5 spreads evenly on the fibreglass braiding 4*ef*, due to which hydrogen peroxide is gasified efficiently. The air guide 7 also shrinks the air space on top of the fibreglass braiding 4*ef* whereby the airflow rate on top of the fibreglass braiding 4*ef* accelerates, a swirling air flow is created, which further speeds up the gasifying of the hydrogen peroxide.

FIG. 17 shows a disinfection device according to the invention the disinfection device body 1 of which is set in a usage space 8, which is a transport/usage briefcase (at best to a device box made of plastic equipped with one or more openable covers)

The usage space 8 has a top side 8*a*, lower side 8*b*, front side 8*c*, rear side 8*d*, left side 8*e*, and right side 8*f*.

The front side 8*c*, rear side 8*d*, left side 8*e* and right side 8*f* of the usage space 8 are designated only for enabling the description of the invention, they could be referred to by other names too, the locations of the parts of the disinfection device may others than those shown in the Figures.

A partition wall 8*g*, to which has shown in FIGS. 18 and 19 openable covers 8*h*, hinged by hinges 8*ga* which covers 8*h* are lockable by one or more known latches to a closed and open position, in the open position the covers 8*h* may be interlocked.

A control apparatus 9 comprises all the control apparatus needed by the disinfection device, and in addition the required connectors to connect electricity, for example, the control apparatus 9 is assembled of known electricity, radio, mobile phone, measurement, control, and communication technology.

A horizontal plane indicator 10 in FIG. 17 is known from bubble levels (an ox-eye bubble level (in the figure in FIG. 17, for example) has a bubble under a convex glass cover which indicates an inclination no matter which compass direction it takes). It may be used for verifying and adjusting the horizontal position of levels, such as tables, with a single glance) a transparent part, from which by means of an air bubble the position of the usage space 8 may be detected, whereby it is easy to adjust the usage space 8 by known adjustment legs (threaded adjustment paws) on the lower side 8*b* (by three adjustment legs 21 shown in FIGS. 17 and 18) to a horizontal plane at best there are only three adjustment paws whereby the usage space 8 does not rock. The horizontal position is important for hydrogen peroxide to drain as planned on the evaporation member 4e and to turn into disinfecting hydrogen peroxide gas.

The horizontal plane indicator 10 may also be an electrical horizontal plane indicator 10 manufactured by a prior art technology, an electrical inclination measurement is used among other in battery powered balancing scooters also referred to with name of e-Driftit E-Driftit is a battery-powered vehicle equipped with two wheels, on which vehicle a person stands, and by tilting a person gets the vehicle to move, as well to steer and to stop the vehicle.

In an accessory space 11 among others a hydrogen peroxide bottle/container may be placed, from which hydrogen peroxide is pumped by one or more known electric liquid pumps by means of one or more draining pipes 6 to one or more draining devices 5. As known, the pumping power of a liquid pump is continuously adjustable, whereby the vaporization of hydrogen peroxide may be adjusted to match the environmental conditions and efficiency requirements.

In FIG. 17, the disinfection device body 1 with all the associated parts is placed close to the front side 8c, but its location need not be this.

The suction channel/suction pipe 12 along which suction air 3 may access the disinfection device. The blowing channel/blowing pipe 12 is at best of flexible and continuous so-called wrinkled pipe the length of which may be continued by pulling on and shortened by pressing on the pipe is known among other things from mobile air-conditioning devices.

The blowing channel/blowing pipe 13 along which hydrogen peroxide gas 14 may access the target to be cleaned. The blowing channel/blowing pipe 13 is at best of flexible and continuous so-called wrinkled pipe the length of which may be continued by pulling on and shortened by pressing on the pipe is known among other things from mobile air-conditioning devices.

A hydrogen peroxide tank 16, which in FIG. 22 is a hydrogen peroxide infusion bottle or bag, from which liquid hydrogen peroxide drains along the draining pipe 6 to the draining device 5 In the draining pipe 6 in FIG. 22 there is a liquid draining adjusting device 16a known from infusion bags of hospitals.

FIG. 24 shows the disinfection device outside a space 17 to be cleaned, the circulation of air to be cleaned and hydrogen peroxide gas 14 takes place controllably by means of a plurality of pipes. Because the disinfection device is outside the space 17 to be cleaned, the device may be safely serviced, adjusted, and used for the duration of the cleaning. In FIG. 24 the suction channels/suction pipes 12 and the blowing channels/blowing pipes 13 are led through an airtight partitioning wall 18 to the space 17 to be cleaned, the pipes may be sealed with known methods, for example with a suitable seal or tape or the like. The partition wall 18 may be of known tarpaulin, placed in door openings or window openings.

FIG. 25 shows that at the top side 1a of the disinfection device body 1 at the blowing end 1e there is one or more pressure blowers 19 in the blowing opening/blowing passage 1g, which boosts the flow of hydrogen peroxide gas 14 in one or more blowing channels/blowing pipes 13.

FIG. 26 shows an inventive disinfection cabinet 15 with the front part open or the front part may have a transparent door such as a glass door. The disinfection cabinet 15 has one or more standardised rack spaces 20 for the disinfection device body 1 where the disinfection device body 1 may be put. It is possible to add the desired number of disinfection devices in the disinfection cabinet 15, which may be referred to as VHP units, catalytic converters, air dryers, heaters, etc. may be added to the disinfection cabinet 15 or similar device as standard-sized modules that have standard connectors for electrical connections as well as air inlet and outlet. The modules are "racks" in the same way as an old DIN-sized car radio—each car has an installation place of the same size, which takes in any radio. The production output of the disinfection cabinet 15 is easy to change as needed, because it is simple to add or remove disinfection devices due to the standard rack spaces 20. That is, output is available as a function of the number of rack spaces 20, because a disinfection cabinet has ready-made rack spaces 20 for the disinfection device bodies 1. FIG. 26 shows shelves 15a for the objects or substances/materials to be cleaned, the shelves 15a are preferably grid shelves or grille shelves whereby hydrogen peroxide gas may access any spot inside the disinfection cabinet 15.

In FIG. 27, the disinfection device bodies 1 are placed in a star shape, as seen from the top, whereby hydrogen peroxide gas 14 may spread well to the space to be cleaned, and correspondingly suction air 3 is centrally sucked into the disinfection devices whereby the desired suction air 3 may be guided from the desired place. Suction air 3 may be centrally blown to all the disinfection device bodies 1 by one blower, or alternatively a plurality of blowers may be used and blow suction air 3 along one or more channels/pipers to a hub of disinfection devices bodies 1, shown in FIG. 27. When channels/pipes are used, it is possible to determine precisely from which place suction air 3 is transferred on the disinfection device bodies 1.

FIG. 28 shows two successive blowers 2. The upper blower 2, called a cold air blower 2a, blows cold air in the direction of the cold air arrow 22 over the evaporation member 4e. The lower blower 2, called a hot air blower 2b, blows air 23 warmed/heated by the warming member 4f, under the evaporation member 4e at a lower rate than the cold air blower 2a above. The blower 2 is the best known axial blower or a similar device moving air, that is, gas. Most preferably filtered air, the filter/cleaner known from the construction industry is not shown in the figures. The gas may be air, nitrogen, argon, or a mixture of the above. The pump 2 is a known pump with which hydrogen superoxide is transferred in liquid form. The pump 2 may be an adjustable-displacement pump or provided with a flow control valve, a separate flow control valve, or a flow control valve internal to the pump.

In FIG. 30, an inward relief valve 24 is a spring-loaded disk valve, which opens when the desired vacuum is reached on the spring side of the valve The inward relief valve 24 has a valve body 24a, a closing disk 24b, an adjusting spring 24c (in FIG. 29 the spring is a compression spring), adjustable screw 24d, and an opening/closing direction arrow 24e In FIG. 30, the vacuum gauge is a known vacuum gauge A vacuum lowers the temperature of vaporization of hydrogen peroxide, whereby the vaporization intensifies The shape of the vacuum valve may be other than that shown in FIG. 30, the most important thing is restricting the incoming air to the disinfection device body 1, that is, air pressure is adjusted in the manner the air pressure of apartments is adjusted.

The density/gas content of the hydrogen peroxide has been measured at the VTT, and the inventive device achieves an output power of 1725 ppm/m3 (particles/million) in a cubic metre, this output power has not yet been achieved with any other disinfection device. Hydrogen peroxide is the only cleaning agent which may be used for disinfecting aeroplanes, because hydrogen peroxide does not leave any residue that could cause electrical short-circuits or other electrical disturbances that could cause a plane to crash mid-flight. The disinfection device comprises one or more tanks 16 and one or more pumps 2 to store and transfer hydrogen peroxide ($H_2O_2$). The pump 2 is an adjustable-displacement pump or in connection with the pump 2 or following it is placed one or more flow control valves by means of which the flow amount of hydrogen peroxide is adjusted for one or more draining devices 5.

The figures show the disinfection method and device to be used for cleaning.

In accordance with the invented method, hydrogen peroxide ($H_2O_2$) is drained/transferred from one or more tanks 16 by a liquid pressure created by one or more pumps or gravity, through one or more draining pipes 6 to one or more draining devices 5, which draining device 5 drains hydrogen peroxide onto one or more evaporation top surfaces 4ea of an evaporation member 4e of a warming/heating device 4, the evaporation top surface 4ea is at an evaporation angle 4ej of 1 to 30 degrees so that the end on the draining device 5 side draining end 4c is higher than a gas discharge end (4d) at the opposite end of the draining device 5 of the warming/heating device 4, whereby hydrogen peroxide spreads by gravity on the evaporation member 4e where the hydrogen peroxide ($H_2O_2$) turns into hydrogen peroxide gas by means of which hydrogen peroxide gas disinfection is performed, the evaporation member 4e consist of one or more braidings or mat or fabric that is either in its entirety or partly a mixture of the aforementioned materials such as nylon or polyester (PET) or PEN fibre (Pentex) or kevlar or technora or twaron or spektri or dyneema or cetran or zylon (PBO) or vecran or fibre glass braiding or carbon fibre or perforated plate or metal net or aluminium oxide.

In accordance with an invented method, hydrogen peroxide ($H_2O_2$) is drained/transferred from one or more tanks 16 by a liquid pressure created by one or more pumps or gravity, through one or more draining pipes 6 to one or more draining devices 5, which draining device 5 drains hydrogen peroxide to one or more onto one or more evaporation top surfaces 4*ea* of an evaporation member 4*e* of a warming/heating device 4, the evaporation top surface 4*ea* is at an evaporation angle 4*ej* of 1 to 30 degrees to the horizontal plane so that the end on the draining device 5 side draining end 4*c* is higher than a gas discharge end 4*d* at the opposite end of the draining device 5 of the warming/heating device 4, whereby hydrogen peroxide spreads by gravity on the evaporation member 4*e* where the hydrogen peroxide ($H_2O_2$) turns into hydrogen peroxide gas by means of which hydrogen peroxide gas disinfection is performed, the end on the draining device 5 side has one or more blowers 2 to blow air in the direction of the evaporation top surface 4*ea* of the evaporation members 4*e* of the warming/heating device 4, the evaporation member 4*e* is the topmost part of the warming/heating device 4, on the evaporation top surface 4*ea* of which on the draining end 4*c* hydrogen peroxide is drained from one or more draining devices 5, the evaporation member 4*e* consists of one or more braidings or mat or fabric that is either in its entirety or partly a mixture of the aforementioned materials such as nylon or polyester (PET) or PEN fibre (Pentex) or kevlar or technora or twaron or spektri or dyneema or cetran or zylon (PBO) or vecran or fibre glass braiding or carbon fibre or perforated plate or metal net or aluminium oxide.

According to an invented method, suction air 3 is sucked by one or more blowers 2 from the gas discharge end 4*d* whereby a vacuum is formed on the evaporation top surface 4*ea*, due to which vacuum hydrogen peroxide turns into hydrogen peroxide gas at a low temperature.

According to an invented method, one or more inward relief valves 24 are used to restrict air from getting inside the disinfection device body 1, whereby as the blower 2 is sucking air from inside the disinfection device body 1, a vacuum is generated inside the disinfection device body 1.

In accordance with an invented method, airflow is faster on the top side of the evaporation top surface 4*ea* of the evaporation member 4*e* of the warming/heating device 4 than on the underside of the evaporation top surface 4*ea*, the disinfection method comprises two blowers 2 one on the other, the higher blower 2, called a cold air blower 2*a*, blows cold air in the direction of the cold air arrow 22 over the evaporation member 4*e*, and the lower blower 2, called a hot air blower 2*b*, blows air 23 warmed/heated by the warming member 4*f*, under the evaporation member 4*e* at a lower rate than the cold air blower 2*a* above.

According to an invented method, the airflow area is reduced by one or more air guides 7 on the top side of the evaporation top surface 4*ea* of the evaporation member 4*e* of the warming/heating device 4 towards the gas discharge end 4*d* whereby the airflow rate is increased/accelerated towards the gas discharge end 4*d*.

According to an invented method, the temperature of the airflow on the top side of the evaporation top surface 4*ea* of the evaporation member 4*e* of the warming/heating device 4 is lower than on the underside of the evaporation top surface 4*ea*.

According to an invented method, the draining device 5 drains hydrogen peroxide to one or more onto one or more evaporation top surfaces 4*ea* of the evaporation member 4*e* of the warming/heating device 4, by means of one or more horizontal plane indicators 10 the evaporation top surface 4*ea* may be adjusted to the correct position in every direction, whereby hydrogen peroxide drains evenly and turns on the evaporation top surface 4*ea* into hydrogen peroxide gas by means of which hydrogen peroxide gas the disinfection is performed.

According to an invented method, the devices of the disinfection method are located in a disinfection device body 1 which disinfection device body 1 is of a standard size and shape, provided with standard, that is, similar connections, due to which a plurality of disinfection device bodies may be interconnected sideways or one on the other, whereby the power of the disinfection method may be selected as desired by placing the desired number of disinfection device bodies 1 in one disinfection device.

According to an invented method, the disinfection device body 1 is a closed box made of metal, stainless steel or aluminium or copper or steel, on the top side 1*a* of which at the suction end 1*d* there is one or more suction opening/suction passages 1*f*, from which suction opening/suction passage 1*f* air/gas may enter inside the disinfection device body 1, said air/gas being used inside the disinfection device body 1 to vaporize hydrogen peroxide ($H_2O_2$), at the blowing end 1*e* of the disinfection device 1 there is one or more blowing opening/blowing passages 1*g* from which blowing opening/blowing passage 1*g* hydrogen peroxide ($H_2O_2$) hydrogen peroxide gas 14 may access the target(s) to be cleaned directly or through a desired pipe or another passage/channel to one or more desired target(s), the suction opening/suction passage 1*f* and the blowing opening/blowing passage 1*g* may be located over, at an end/ends, below, or by the side of the disinfection device body 1, the location may be freely chosen as needed because the blower 2 carries out the circulation of air or gas of mixture of gas and airs, one or more suction channels/suction pipes 12 and blowing channels/blowing pipes 13 may be fixed to the blowing opening/blowing passage 1g.

According to an invented method, one or more blowers 2 to blow clean air or to circulate air to be purified, the blower/blowers (2) suck suction air (3) into the disinfection device body 1 from one or more suction openings/suction passages (1f) at the suction end (1d), the blower 2 is an axial blower or a similar device moving gas/air which sucks gas/air in the direction of the arrow 3, the air may be filtered by using an air filter/purifier, the suction air 3 which may be air, oxygen, argon or a mixture of the aforementioned, the blower/blowers 2 blow suction air 3 almost horizontally, as seen from the side, at an evaporation angle 4ej of 1 to 30 degrees, to a hydrogen peroxide draining end 4c of the warming/heating device 4.

According to an invented method, the evaporation member 4e is crosswise woven braiding, which may also be referred to as a mat or fabric, the density of the evaporation member 4e is such that air may pass through the evaporation member 4e, the thickness of the evaporation member 4e is 0.5 to 3 mm depending on the surface area of the evaporation member 4e.

According to an invented method, the disinfection device bodies 1 are placed in a star shape, as seen from above, whereby hydrogen peroxide gas 14 may spread well to the space to be cleaned, and correspondingly suction air 3 is centrally sucked into the disinfection devices whereby the desired suction air 3 may be guided from the desired place.

According to an invented method, the suction channel/suction pipe 12, along which suction air 3 may access the disinfection device, is preferably flexible and continuous so-called wrinkled pipe whose length may be increased by pulling on it and shortened by pressing on it, the pipe is known from mobile air-conditioning devices, for example, and/or the blowing channel/blowing pipe 13 is preferably flexible and continuous so-called wrinkled pipe whose length may be increased by pulling on it and shortened by pressing on it.

An invented disinfection device in which hydrogen peroxide ($H_2O_2$) is drained/transferred from one or more tanks 16 by a liquid pressure created by one or more pumps or gravity, through one or more draining pipes 6 to a draining device body 1 which has one or more draining devices, by means or which draining device 5 hydrogen peroxide may be drained to one or more onto one or more evaporation top surfaces 4ea of an evaporation member 4e of a warming/heating device 4, the evaporation top surface 4ea is at an evaporation angle 4ej of 1 to 30 degrees to the horizontal plane so that the end on the draining device 5 side draining end 4c is higher than a gas discharge end 4d at the opposite end of the draining device 5 of the warming/heating device 4, whereby hydrogen peroxide spreads by gravity on the evaporation member 4e where the hydrogen peroxide ($H_2O_2$) turns into hydrogen peroxide gas by means of which hydrogen peroxide gas disinfection is performed, the end on the draining device 5 side has one or more blowers 2 to blow air in the direction of the evaporation top surface 4ea of the evaporation member 4e of the warming/heating device 4, the evaporation member 4e is the topmost part of the warming/heating device 4, on the evaporation top surface 4ea of which on the draining end 4c hydrogen peroxide is drained from one or more draining devices 5, the evaporation member 4e consists of one or more braidings or mat or fabric that is either in its entirety or partly a mixture or the aforementioned materials such as nylon or polyester (PET) or PEN fibre (Pentex) or kevlar or technora or twaron or spektri or dyneema or cetran or zylon (PBO) or vecran or fibre glass braiding or carbon fibre or perforated plate or metal net or aluminium oxide.

An invented disinfection device in which the evaporation member 4e is the topmost part of the warming/heating device 4, on the evaporation top surface 4ea of which on the draining end 4c hydrogen peroxide is drained from one or more draining devices 5, there is one or more nets 4ei on the evaporation member 4ei.

An invented disinfection device in which the net 4ei is a net made of metal wire, with a mesh size of 0.3 to 5 mm and wire thickness 0.3 to 1.0 mm.

An invented disinfection device in which one or more inward relief valves 24 are used to restrict air from getting inside the disinfection device body 1, whereby as the blower 2 is sucking air from inside the disinfection device body 1, a vacuum is generated inside the disinfection device body 1.

An invented disinfection device in which the inward relief valve 24 is adjustable whereby the desired vacuum may be had inside the disinfection device body 1, the vacuum being measurable by one or more vacuum gauges 25.

AN EXAMPLE OF USING THE INVENTION

The cleaning of surfaces to be disinfected is carried out by one or more invented disinfection devices. Before disinfection is started, the targets to be disinfected must be mechanically cleaned, by a prior art technology, as best as possible, for example foodstuff or other porous targets may be difficult to clean mechanically.

The disinfection device/devices is/are placed to a closed space, the normal room height, for example, 2.5 m container or room. The room must be possible to be well ventilated, to which a blower and filter unit, known from ventilation of buildings, are connected. In the room, a plurality of air condition management devices are placed to stabilise the humidity level, which are devices known from the management of air condition of premises of buildings, including laboratories where air temperature, humidity, and purity are strictly managed and controlled. The disinfection device/devices are placed in the room. The disinfection device/devices are activated by remote control, using a prior art technology. The disinfection process is automatic and, depending on the room size, takes from a few hours to a day or days, the duration of the process depends on the target being cleaned. After the disinfection, the room is ventilated through known filters to outside air. The cleaned devices/targets are ready for transfer for further measures. The quality assurance documentation may be had from VTT Technical Research Centre of Finland Ltd, for example.

The invented disinfection device may be manufactured by known methods from known materials, most advantageously from metals.

It is apparent to a person skilled in the art that the above exemplary embodiments are rather simple in structure and operation for the purposes of illustration of the description. By following the model shown in this patent application, it is possible to construct different structural solutions that utilise the inventive idea disclosed in this patent application. The invention is not restricted to the alternatives disclosed in the above, but many variations are possible within the scope of the inventive idea defined by the attached claims.

The invention claimed is:

1. A disinfection method for use for cleaning, the method comprising:
providing one or more tanks to store liquid hydrogen peroxide ($H_2O_2$);

providing a warming/heating device comprising an evaporation member that is a topmost part of the warming/heating device and comprises one or more evaporation top surfaces, a warming member connected underside of the one or more evaporation top surfaces and configured to warm up the one or more evaporation top surfaces, the warming member being equipped with warming ribs and a warmer, the warming/heating device having a draining end and a gas discharge end opposite the draining end, one or more draining devices being provided at the draining end of the warming/heating device, the one or more evaporation top surfaces being at an evaporation angle of 1-30 degrees relative to horizontal so that the draining end of the warming/heating device is higher than the gas discharge end of the warming/heating device, the evaporation member consisting of: one or more braidings, mat, fabric, or mixture thereof;

draining hydrogen peroxide from the one or more tanks by a liquid pressure created by one or more pumps or gravity through one or more draining members to a draining device body comprising the one or more draining devices;

blowing, by one or more blowers, air in the direction of the one or more evaporation top surfaces;

draining hydrogen peroxide by the one or more draining devices onto the one or more evaporation top surfaces, to the draining end, for spreading hydrogen peroxide by gravity on the evaporation member and turning the hydrogen peroxide liquid into hydrogen peroxide gas by means of which hydrogen peroxide gas disinfection is performed.

2. The disinfection method of claim 1, wherein the one or more blowers comprise a cold air blower configured to blow cold air over the evaporation member, and a hot air blower configured to blow air warmed/heated by a warming member of the warming/heating device under the evaporation member at a lower rate than the cold air blower, the cold air blower being located above the hot air blower.

3. The disinfection method of claim 1, wherein the airflow area is reduced by one or more air guides on the top side of the one or more evaporation top surfaces towards the gas discharge end, increasing the airflow rate towards the gas discharge end.

4. The disinfection method of claim 1, wherein the position(s) of the one or more evaporation top surfaces is/are adjustable by one or more horizontal plane indicators.

5. A disinfection device for use for cleaning, comprising:
one or more tanks configured to store liquid hydrogen peroxide ($H_2O_2$);
one or more draining members;
a draining device body comprising one or more draining devices;
a warming/heating device comprising an evaporation member that is a topmost part of the warming/heating device and comprises one or more evaporation top surfaces, a warming member connected underside of the one or more evaporation top surfaces and configured to warm up the one or more evaporation top surfaces, the warming member being equipped with warming ribs and a warmer, the warming/heating device having a draining end and a gas discharge end opposite the draining end, the one or more draining devices being provided at the draining end of the warming/heating device, the one or more evaporation top surfaces being at an evaporation angle of 1-30 degrees relative to horizontal so that the draining end of the warming/heating device is higher than the gas discharge end of the warming/heating device, the evaporation member consisting of: one or more braidings, mat, fabric, or mixture thereof;

one or more blowers configured to blow air in the direction of the one or more evaporation top surfaces;

wherein in the disinfection device, hydrogen peroxide is configured to be drained from the one or more tanks by a liquid pressure created by one or more pumps or gravity through the one or more draining members to the draining device body and by the one or more draining devices onto the one or more evaporation top surfaces, to the draining end, for spreading hydrogen peroxide by gravity on the evaporation member and turning hydrogen peroxide liquid into hydrogen peroxide gas by means of which hydrogen peroxide gas disinfection is performed.

6. The disinfection device of claim 5, further comprising a disinfection device body and one or more inward relief valves configured to restrict air from getting inside the disinfection device body.

7. The disinfection device of claim 6, further comprising one or more vacuum gauges configured to measure a vacuum level inside the disinfection device body.

8. The disinfection device of claim 6, wherein the one or more evaporation top surfaces comprise one or more metal nets.

9. The disinfection device of claim 7, wherein the one or more evaporation top surfaces comprise one or more metal nets.

10. The disinfection device of claim 5, wherein the one or more blowers comprise a cold air blower configured to blow cold air over the evaporation member, and a hot air blower configured to blow air warmed/heated by the warming member of the warming/heating device under the evaporation member at a lower rate than the cold air blower, the cold air blower being located above the hot air blower.

11. The disinfection device of claim 5, further comprising one or more air guides on the top side of the one or more evaporation top surfaces configured to reduce an airflow area towards the gas discharge end and increasing an airflow rate towards the gas discharge end.

12. The disinfection device of claim 5, wherein the position(s) of the one or more evaporation top surfaces is/are adjustable by one or more horizontal plane indicators.

* * * * *